United States Patent [19]
Jones et al.

[11] Patent Number: 6,071,708
[45] Date of Patent: Jun. 6, 2000

[54] MORPHOGENIC PROTEIN COMPOSITIONS OF MATTER

[75] Inventors: William K. Jones, Brookline; Ronald F. Tucker, Holliston; David C. Rueger, Hopkinton; Hermann Oppermann, Medway; Engin Ozkaynak, Milford; Thangavel Kuberasampath, Medway, all of Mass.

[73] Assignee: Stryker Biotech, Natick, Mass.

[21] Appl. No.: 08/889,419

[22] Filed: Jul. 8, 1997

Related U.S. Application Data

[60] Continuation of application No. 08/459,346, Jun. 2, 1995, Pat. No. 5,834,179, which is a division of application No. 08/402,542, Mar. 13, 1995, which is a continuation of application No. 08/040,510, Mar. 31, 1993, abandoned, which is a continuation-in-part of application No. 08/029,335, Mar. 4, 1993, abandoned, and a continuation-in-part of application No. 08/027,070, Mar. 4, 1994, abandoned, and a continuation-in-part of application No. 07/971,091, Nov. 3, 1992, abandoned, and a continuation-in-part of application No. 07/946,235, Sep. 16, 1992, abandoned, and a continuation-in-part of application No. 07/938,336, Aug. 28, 1992, abandoned, and a continuation-in-part of application No. 07/923,780, Jul. 31, 1992, abandoned, which is a continuation-in-part of application No. 07/752,857, Aug. 30, 1991, abandoned, and a continuation-in-part of application No. 07/752,764, Aug. 30, 1991, abandoned, which is a continuation-in-part of application No. 07/667,274, Mar. 11, 1991, abandoned.

[51] Int. Cl.$^7$ .................................................. G01N 33/53
[52] U.S. Cl. ............................................ 435/7.1; 435/536
[58] Field of Search ............................. 435/7.1; 436/536

[56] References Cited

U.S. PATENT DOCUMENTS

| | | |
|---|---|---|
| 4,294,753 | 10/1981 | Urist . |
| 4,455,256 | 6/1984 | Urist . |
| 4,465,669 | 8/1984 | Wissler et al. ........................... 424/177 |
| 4,857,456 | 8/1989 | Urist ............................................. 435/7 |
| 5,106,748 | 4/1992 | Wozney et al. ....................... 435/252.3 |
| 5,141,905 | 8/1992 | Rosen et al. ........................... 435/69.1 |
| 5,168,050 | 12/1992 | Hammonds, Jr. et al. ............ 435/69.1 |
| 5,393,739 | 2/1995 | Bentz et al. ................................ 514/12 |

FOREIGN PATENT DOCUMENTS

| | | |
|---|---|---|
| WO89/09787 | 10/1989 | WIPO . |
| WO89/09788 | 10/1989 | WIPO . |

OTHER PUBLICATIONS

Bowie et al., "Deciphering the Message in Protein Sequences: Tolerance to Amino Acid Substitutions", *Science*, 247:1306–1310 (1987).

Celeste et al., "Identification of Transforming Growth Factor β Family Members Present in Bone–Inductive Protein Purified from Bovine Bone", Proc. Natl. Acad. Aci., USA, 87:9843–9847 (1990).

Gentry et al., "The Pro Domain of Pre–Pro–Transforming Growth Factor β1 When Independently Expressed is a Functional Binding Protein for the Mature Growth Factor", *Biochemistry*, 29:6851–6857 (1990).

Hammonds Jr., et al., "Bone–Inducing Activity of Mature BMP–2b Produced from a Hybrid BMP–2a/2b Precursor", *Mol. Endocrin.* 5:149–155 (1991).

Israel et al., "Expression and Characterization of Bone Morphogenic Protein–2 in Chinese Hamster Ovary Cells", Growth Factors, 7: 139–150 (1992).

Lee, "Expression of Growth/Differentiation Factor 1 in the Nervous System: Conservation of a Bicistronic Structure", Proc. Natl. Acad. Sci., 88: 4250–4254 (1991).

Lyons et al., "Vgr–1, a Mammalian Gene Related to Xenopus Vg–1, is a Member of the Transforming Growth Factor β Gene Superfamily", Proc. Natl. Acad. Sci., USA, 86: 4554–4558 (1989).

Lyons et al., "Transforming Growth Factors and the Regulation of Cell Proliferation", *Eur. J. Biochem.* 187:467–473 (1990).

Massague, "The TGF–β Family of Growth and Differentiation Factors", *Cell,* 49:437–438 (1987).

Ngo et al., "Computational Complexity, Protein Structure Prediction, and the Levinthal Paradox", *The Protein Folding Problem and Tertiary Structure Prediction,* Ch. 14, pp./ 492–494 (1994).

Özkaynak et al., "OP–1 cDNA Encodes an Osteogenic Protein in the TGF–β Family", *The EMBO J.,* 9:2085–2093 (1990).

Panganiban et al., "Biochemical Characterization of the Drosophila dpp Protein, a Member of the Transforming Growth Factor β Family of Growth Factors", *Mol. and Cellul. Biol.,* 10:2669–2677 (1990).

Pepinsky et al., "Proteolytic Processing of Mullerian Inhibiting Substance Produces a Transforming Growth Factor–β–like Fragment", *J. Biol. Chem.* 263:18961–18964 (1988).

Rudinger, "Characteristics of the Amino Acids as Components of a Peptide Hormone Sequence", *Peptide Hormones,* pp. 1–7 (1976).

Turing, "The Chemical Basis of Morphogenesis", *Phil. Trans. Roy. Soc.* B 237:39–84 (1952).

Urist et al., "Radioimmunoassay of Bone Morphogenetic Protein in Serum: A Tissue–Specific Parameter of Bone Metabolism", *Pro. Soc. for Exper. Bio. Med.,* 176:472–475 (1984).

Wakefield et al., "Recombinant Latent Transforming Growth Factorβ1, and a Different Tissue Distribution", *J. of Clin. Invest.,* 86:1976–1984 (1990).

Wang et al., "Purification and Characterization of Other Distinct Bone–Inducing Factors", Proc. Natl. Acad. Sci., USA, 85:9484–9488 (1988).

Wang et al., "Recombinant Human Bone Morphogenetic Protein Induces Bone formation", Proc. Natl. Acad. Sci., 87:2220–2224 (1990).

(List continued on next page.)

*Primary Examiner*—Sheela Huff
*Attorney, Agent, or Firm*—Testa, Hurwitz & Thibeault, LLP

[57] ABSTRACT

Disclosed are novel compositions of morphogenic proteins constituting soluble forms of these proteins, antibodies that distinguish between soluble and mature forms, and method for producing these morphogenic proteins and antibodies.

8 Claims, 2 Drawing Sheets

OTHER PUBLICATIONS

Weeks et al., "A Maternal mRNA Localized to the Vegetal Hemisphere in Xenopus Eggs Codes for a Growth Factor Related to TGF-β" *Cell* 51:861–867 (1987).

Wharton et al., "Drosphila 60A Gene, Another Transforming Growth Factor β Family Member, is Closely Related to Human Bone Morphogenetic Proteins", Proc. Natl. Acad. Sci., 88:9214–9218 (1991).

Wilkins, "What's in a (biological) term? Frequently, a Great Deal of Ambiguity", *BioEssays,* 17:375–377 (1995).

Wozney et al., "Novel Regulators of Bone Formation: Molecular Clones and Activities" *Science,* 242: 1528–1533 (1988).

```
OP-2:  RAPRSQQPFVVTFFRASPSPIRTPRAVRPLRRRQPKKSNELPQANRLPGIFDDDVHGSHGRQVC
OP-1:                          RSIRSTGSKQRSQNRSKTPKNQEALRMANVAENSSSDQRQAC
Vgr-1:                         RTTRSASSRRRQQSRNRSTQSQDVSRGSGSSDYNGSELKTAC
BMP-5:                         RSVRAANKRKNQNRNKSSSHQDSSRMSSVGDYNTSEQKQAC
60A:                            RSKRSASHPRKRKKSVSPNNVPLLEPMESTRSC
DPP:                            RSIRDVSGGEGGKGGGRNKRHARRPTRRKNHDDTC
BMP-2: RHVRISRSLHQDEHSWSQIRPLLVTFGHDGKGHPLHK--REKRQAKH--KQRKRLKSSC
BMP-4: RISRSLPQGSGNWAQLRPLLVTFGHDGRGHALTRRRRAKRSPKHHSQRARKKNKNC
Vg-1:                                           RCKRPRKRSYSKLPFTASNIC
BMP-3: RKKRSTGVLLPLQ..........KSKNKKQRKGPHRKSQTLQFDEQTLKKARRKQWIEPRNC
```

Fig. 2

MORPHOGENIC PROTEIN COMPOSITIONS OF MATTER

This application is a continuation of application U.S. Ser. No. 08/459,346, filed Jun. 2, 1995, now U.S. Pat. No. 5,834,179, which is a divisional of (1) copending application U.S. Ser. No. 08/402,542, filed on Mar. 13, 1995, which is a continuation of U.S. Ser. No. 08/040,510, filed Mar. 31, 1993, now abandoned; which is a continuation-in-part of U.S. Ser. No. 08/029,335, filed Mar. 4, 1993, now abandoned; (2) U.S. Ser. No. 08/027,070, filed Mar. 4, 1993, now abandoned; (3) U.S. Ser. No. 07/971,091, filed Nov. 3, 1992, now abandoned; (4) U.S. Ser. No. 07/946,235, filed Sep. 16, 1992, now abandoned; (5) U.S. Ser. No. 07/938,336, filed Aug. 28, 1992, now abandoned; (6) U.S. Ser. No. 07/923,780, filed Jul. 31, 1992, now abandoned, which is a continuation-in-part of U.S. Ser. No. 07/752,857, filed Aug. 30, 1991, now abandoned; and (7) U.S. Ser. No. 07/752,764, filed Aug. 30, 1991, now abandoned, which is a continuation-in-part of U.S. Ser. No. 07/667,274, filed Mar. 11, 1991, now abandoned. The disclosures of these applications are incorporated herein by reference.

FIELD OF THE INVENTION

The present invention relates generally to morphogenic proteins and, more particularly, to compositions having improved solubility in aqueous solvents.

BACKGROUND OF THE INVENTION

Morphogenic proteins ("morphogens") are well known and described in the art. See, for example, U.S. Pat. Nos. 4,968,590; 5,011,691; 5,018,753; PCT US92/01968 and PCT US92/07432; as well as various articles published in the scientific literature, including Ozkaynak et al. (1992) *J. Biol. Chem.* 267:25220–25227 and Ozkaynak et al. (1991) *Biochem. Biophys. Res. Comm.* 179:116–123. The art has described how to isolate morphogenic proteins from bone, how to identify genes encoding these proteins and how to express them using recombinant DNA technology. The morphogenic proteins are capable of inducing endochondral bone formation and other tissue formation in a mammal when they are properly folded, dimerized and disulfide bonded to produce a dimeric species having the appropriate three dimensional conformation. The proteins have utility in therapeutic applications, either by direct or systemic administration. Where bone induction is desired, for example, the morphogen typically is provided to the desired site for bone formation in a mammal in association with a suitable matrix having the appropriate conformation to allow the infiltration, proliferation and differentiation of migrating progenitor cells. The morphogenic protein adsorbed to the surfaces of a suitable matrix is generally referred to in the art as an osteogenic device. The proteins can be isolated from bone or, preferably, the gene encoding the protein is produced recombinantly in a suitable host cell.

The morphogen precursor polypeptide chains share a common structural motif, including a N-terminal signal sequence and pro region, both of which are cleaved to produce a mature sequence, capable of disulfide bonding and comprising an N-terminal extension and a C-terminal domain whose amino acid sequence is highly conserved among members of the family. In their mature dimeric forms, the morphogens typically are fairly insoluble under physiological conditions. Increasing the solubility of these proteins has significant medical utility as it would enhance systemic administration of morphogens as therapeutics. Various carrier proteins, including serum albumin and casein are known to increase the solubility of morphogens (see, for example, PCT US92/07432). PCT US92/05309 (WO 93/00050) discusses the use of various solubilizing agents, including various amino acids and methyl esters thereof, as well as guanidine, sodium chloride and heparin, to increase the solubility of mature dimeric BMP2.

Improved methods for the recombinant expression of morphogenic proteins is an ongoing effort in the art. It is an object of this invention to provide an improvement in the methods for producing and purifying morphogenic proteins having high specific activity, and for formulating compositions and osteogenic devices comprising these proteins. Another object is to provide soluble forms of morphogenic proteins consisting essentially of amino acid sequences derived from morphogenic proteins. Another object is to provide formulations which stabilize the soluble complex of morphogenic proteins. Still another object is to provide means for distinguishing between soluble forms of the protein and the mature morphogenic species, to provide means for quantitating the amounts of these proteins in a fluid, including a body fluid, such as serum, cerebro-sprinal fluid or peritoneal fluid, and to provide polyclonal and monoclonal antibodies capable of distinguishing between these various species.

Another object is to provide antibodies and biological diagnostic assays for monitoring the concentration of morphogens and endogenous anti-morphogen antibodies present in a body fluid and to provide assays for detecting fluctuations in the concentrations of these proteins in a body fluid. U.S. Pat. No. 4,857,456 and Urist et al. (1984) *Proc. Soc. Exp. Biol. Med.* 176:472–475 describe a serum assay for detecting a protein purported to be a bone morphogenetic protein. The protein is not a member of the morphogen family of proteins described herein, differing in molecular weight, structural characteristics and solubility from these proteins.

SUMMARY OF THE INVENTION

It has now been discovered that morphogenic protein secreted into cultured medium from mammalian cells contains as a significant fraction of the secreted protein a soluble form of the protein, and that this soluble form comprises the mature dimeric species, including truncated forms thereof, noncovalently associated with at least one, and preferably two pro domains. It further has been discovered that antibodies can be used to discriminate between these two forms of the protein. These antibodies may be used as part of a purification scheme to selectively isolate the mature or the soluble form of morphogenic protein, as well as to quantitate the amount of mature and soluble forms produced. These antibodies also may be used as part of diagnostic treatments to monitor the concentration of morphogenic proteins in solution in a body and to detect fluctuations in the concentration of the proteins in their various forms. The antibodies and proteins also may be used in diagnostic assays to detect and monitor concentrations of endogenous anti-morphogen antibodies to the various forms of these proteins in the body.

An important embodiment of the invention is a dimeric protein comprising a pair of polypeptide subunits associated to define a dimeric structure having morphogenic activity. As defined herein and in parent, related applications, morphogens generally are capable of all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells.

Each of the subunits of the dimeric morphogenic protein comprises at least the 100 amino acid peptide sequence having the pattern of seven or more cysteine residues characteristic of the morphogen family. Preferably, at least one of the subunits comprises the mature form of a subunit of a member of the morphogen family, or an allelic, species, mutant or chimeric variant thereof, noncovalently complexed with a peptide comprising part or all of a pro region of a member of the morphogen family, or an allelic, species, chimeric or other sequence variant thereof. The pair of subunits and one or, preferably, two pro region peptides, together form a complex which is more soluble in aqueous solvents than the uncomplexed pair of subunits.

Preferably, both subunits comprise a mature form of a subunit of a member of the morphogen family or an allelic, species, chimeric, or other sequence variant thereof, and both subunits are noncovalently complexed with a pro region comprising peptide, or a fragment thereof. Most preferably, each subunit is the mature form of human OP-1, or a species, allelic or other mutant variant thereof, and the pro region is the entire or partial sequence of the pro region of human OP-1, or a species, allelic or other mutant variant thereof. Preferred pro regions are full length forms of the pro region. Pro region fragments preferably include the first 18 amino acids of the pro sequence. Other useful pro region fragments are truncated sequences of the intact pro region sequence, the truncation occurring at the proteolytic cleavage site Arg-Xaa-Xaa-Arg (SEQ ID NO: 23).

As used herein, the mature form of a morphogen protein subunit includes the intact C-terminal domain and intact or truncated forms of the N-terminal extensions. For example, useful mature forms of OP-1 include dimeric species defined by residues 293–431 of Seq ID No. 1, as well as truncated sequences thereof, including sequences defined by residues 300–431, 313–431, 315–431, 316–431 and 318–431. Note that this last sequence retains only about the last 10 residues of the N-terminal extension sequence. FIG. 2 presents the N-terminal extensions for a number of preferred morphogen sequences. Canonical Arg-Xaa-Xaa-Arg (SEQ ID NO: 23) cleavage sites where truncation may occur are boxed or underlined in the figure. As will be appreciated by those skilled in the art, mature dimeric species may include subunit combinations having different N-terminal truncations.

Other soluble forms of morphogens include dimers of the uncleaved pro forms of these proteins (see below), as well as "hemi-dimers" wherein one subunit of the dimer is an uncleaved pro form of the protein, and the other subunit comprises the mature form of the protein, including truncated forms thereof, preferably noncovalently associated with a cleaved pro domain.

The soluble proteins of this invention are useful in the formation of therapeutic compositions for administration to a mammal, particularly a human, and for the development of biological assays for monitoring the concentration of these proteins and endogenous antibodies to these proteins in body fluids, including, but not limited to, serum, cerebrospinal fluid and peritoneal fluid.

The foregoing and other objects, features and advantages of the present invention will be made more apparent from the following detailed description of the invention.

BRIEF DESCRIPTION OF THE DRAWINGS

FIG. 2 lists the sequences of the N-terminal extensions of the mature forms of various morphogens SEQ ID NO: 5, 1, 14, 18, 16, 12, 10, 11, 13, 17, respectively.

DETAILED DESCRIPTION

Figure 1:
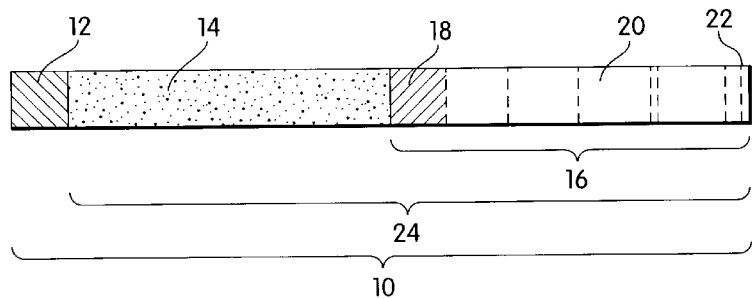
FIG. 1 is a schematic representation of a morphogen polypeptide chain as expressed from a nucleic acid encoding the sequence, wherein the cross-hatched region represents the signal sequence; the stippled region represents the pro domain; the hatched region represents the N-terminus ("N-terminal extension") of the mature protein sequence; and the open region represents the C-terminal region of the mature protein sequence defining the conserved seven cysteine domain, the conserved cysteines being indicated by vertical hatched lines.

A soluble form of morphogenic proteins now has been discovered wherein the proteins consist essentially of the amino acid sequence of the protein. The soluble form is a non-covalently associated complex comprising the pro domain or a fragment thereof, noncovalently associated or complexed with a dimeric protein species having morphogenic activity, each polypeptide of the dimer having less than 200 amino acids and comprising at least the C-terminal six, and preferably seven cysteine skeleton defined by residues 335–431 and 330–431 respectively, of Seq. ID No. 1. Preferably, the polypeptide chains of the dimeric species comprise the mature forms of these sequences, or truncated forms thereof. Preferred truncated forms comprise the intact C-terminal domain and at least 10 amino acids of the N-terminal extension sequence. The soluble forms of these morphogenic proteins may be isolated from cultured cell medium, a mammalian body fluid, or may be formulated in vitro.

In vivo, under physiological conditions, the pro domain may serve to enhance the transportability of the proteins, and/or to protect the proteins from proteases and scavenger molecules, including antibodies. The pro domains also may aid in targeting the proteins to a particular tissue and/or to present the morphogen to a morphogen cell surface receptor by interaction with a co-receptor molecule. The isolated proteins may be used in therapeutic formulations, particularly for oral or parenteral administration, and in the development of diagnostic assays to monitor the level of endogenous morphogens and endogenous anti-morphogen antibodies.

Detailed descriptions of the utility of these morphogens in therapies to regenerate lost or damaged tissues and/or to inhibit the tissue destructive effects of tissue disorders or diseases, are provided in co-pending U.S. patent application Ser. No. 07/752,764, filed Aug. 31, 1991 now abandoned in favor of continuation application U.S. Ser. No. 08/404,113; U.S. Ser. No. 07/938,336, filed Aug. 28, 1992, now abandoned in favor of continuation application U.S. Ser. No. 08/445,467; U.S. Ser. No. 07/923,780, filed Jul. 31, 1992, now abandoned in favor of continuation application U.S. Ser. No. 08/432,883; U.S. Ser. No. 07/945,292, filed Sep. 15, 1992, now abandoned in favor of continuation application U.S. Ser. No. 08/271,556; U.S. Ser. No. 07/945,285, filed Sep. 15, 1992, now abandoned in favor of continuation application U.S. Ser. No. 08/155,343; U.S. Ser. No. 07/938, 337, filed Aug. 28, 1992, now abandoned in favor of continuation application U.S. Ser. No. 08/480,515; U.S. Ser. No. 07/922,813, filed Jul. 31, 1992, now abandoned in favor of continuation application U.S. Ser. No. 08/260,675; U.S. Ser. No. 07/946,235, filed Sep. 16, 1992, now abandoned in favor of continuation application U.S. Ser. No. 08/278,730; U.S. Ser. No. 07/946,238, filed Sep. 16, 1992, now abandoned in favor of continuation application U.S. Ser. No. 08/445,468; U.S. Ser. No. 07/945,286, filed Sep. 15, 1992, now abandoned in favor of continuation application U.S. Ser. No. 08/461,397; and U.S. Ser. No. 07/971,071, filed Nov. 3, 1992, now abandoned in favor of continuation application U.S. Ser. No. 08/480,528, the disclosures of which are incorporated herein by reference. Morphogens, including the soluble morphogen complexes of this invention, are envisioned to have particular utility as part of therapies for regenerating lost or damaged bone, dentin, periodontal, liver, cardiac, lung and nerve tissue, as well as for protecting these tissues from the tissue destructive effects associated with an immunological response. The proteins also are anticipated to provide a tissue protective effect in the treatment of metabolic bone disorders, such as osteoporosis, osteomalacia and osteosarcoma; in the treatment of liver disorders, including cirrhosis, hepatitis, alcohol liver disease and hepatic encephalopathy; and in the treatment or prevention of ischemia reperfusion-associated tissue damage, particularly to nerve or cardiac tissue.

Presented below are detailed descriptions of useful soluble morphogen complexes of this invention, as well as how to make and use them.

I. Useful Soluble Morphogen Complexes—Protein Considerations

Among the morphogens useful in this invention are proteins originally identified as osteogenic proteins, such as the OP-1, OP-2 and CBMP2 proteins, as well as amino acid sequence-related proteins such as DPP (from Drosophila), Vgl (from Xenopus), Vgr-1 (from mouse, see U.S. Pat. No. 5,011,691 to Oppermann et al.), GDF-1 (from mouse, see Lee (1991) *PNAS* 88:4250–4254), 60A protein (from Drosophila, see Wharton et al. (1991) *PNAS* 88:9214–9218), and the recently identified OP-3.

The members of this family, which are a subclass of the TGF-β super-family of proteins, share characteristic structural features, represented schematically in FIG. 1, as well as substantial amino acid sequence homology in their C-terminal domains, including a conserved seven cysteine structure. As illustrated in the figure, the proteins are translated as a precursor polypeptide sequence 10, having an N-terminal signal peptide sequence 12, (the "pre pro" region, indicated in the figure by cross-hatching), typically less than about 30 residues, followed by a "pro" region 14, indicated in the figure by stippling, and which is cleaved to yield the mature sequence 16. The mature sequence comprises both the conserved C-terminal seven cysteine domain 20, and an N-terminal sequence 18, referred to herein as an N-terminal extension, and which varies significantly in sequence between the various morphogens. Cysteines are represented in the figure by vertical hatched lines 22. The polypeptide chains dimerize and these dimers typically are stabilized by at least one interchain disulfide bond linking the two polypeptide chain subunits.

The signal peptide is cleaved rapidly upon translation, at a cleavage site that can be predicted in a given sequence using the method of Von Heijne ((1986) *Nucleic Acids Research* 14:4683–4691.) The "pro" form of the protein subunit, 24, in FIG. 1, includes both the pro domain and the mature domain, peptide bonded together. Typically, this pro form is cleaved while the protein is still within the cell, and the pro domain remains noncovalently associated with the mature form of the subunit to form a soluble species that appears to be the primary form secreted from cultured mammalian cells. Typically, previous purification techniques utilized denaturing conditions that disassociated the complex.

Other soluble forms of morphogens secreted from mammalian cells include dimers of the pro forms of these proteins, wherein the pro region is not cleaved from the mature domain, and "hemi-dimers", wherein one subunit comprises a pro form of the polypeptide chain subunit and the other subunit comprises the cleaved mature form of the polypeptide chain subunit (including truncated forms thereof), preferably noncovalently associated with a cleaved pro domain.

The isolated pro domain typically has a substantial hydrophobic character, as determined both by analysis of the sequence and by characterization of its properties in solution. The isolated pro regions alone typically are not significantly soluble in aqueous solutions, and require the presence of denaturants, e.g., detergents, urea, guanidine HCl, and the like, and/or one or more carrier proteins. Accordingly, without being limited to any given theory, the non-covalent association of the cleaved pro region with the mature morphogen dimeric species likely involves interaction of a hydrophobic portion of the pro region with a corresponding hydrophobic region on the dimeric species, the interaction of which effectively protects or "hides" an otherwise exposed hydrophobic region of the mature dimer from exposure to aqueous environments, enhancing the affinity of the mature dimer species for aqueous solutions.

Morphogens comprise a subfamily of proteins within the TGF-β superfamily of structurally related proteins. Like the morphogens described herein, TGF-β also has a pro region which associates non-covalently with the mature TGF-β protein form. However, unlike the morphogens, the TGF-β pro region contains numerous cysteines and forms disulfide bonds with a specific binding protein. The TGF-β1 pro domain also is phosphorylated at one or more mannose residues, while the morphogen pro regions typically are not.

Useful pro domains include the full length pro regions described below, as well as various truncated forms hereof, particularly truncated forms cleaved at proteolytic Arg-Xaa-Xaa-Arg (SEQ ID NO: 23) cleavage sites. For example, in OP-1, possible pro sequences include sequences defined by residues 30–292 (full length form); 48–292; and 158–292. Soluble OP-1 complex stability is enhanced when the pro region comprises the full length form rather than a truncated form, such as the 48–292 truncated form, in that residues 30–47 show sequence homology to the N-terminal portions of other morphogens, and are believed to have particular utility in enhancing complex stability for all morphogens. Accordingly, currently preferred pro sequences are those encoding the full length form of the pro region for a given morphogen (see below). Other pro sequences contemplated to have utility include biosynthetic pro sequences, particularly those that incorporate a sequence derived from the N-terminal portion of one or more morphogen pro sequences.

Table I, below, describes the various preferred morphogens identified to date, including their nomenclature as used herein, the sequences defining the various regions of the subunit sequences, their Seq. ID references, and publication sources for their nucleic acid and amino acid sequences. The disclosure of these publications is incorporated herein by reference. The mature protein sequences defined are the longest anticipated forms of these sequences. As described above, shorter, truncated forms of these sequences also are contemplated. Preferably, truncated mature sequences include at least 10 amino acids of the N-terminal extension. FIG. 2 lists the N-terminal extensions for a number of the preferred morphogen sequences described below. Arg-Xaa-Xaa-Arg (SEQ ID NO: 23) cleavage sites that may yield truncated sequences of the mature subunit form are boxed or underlined in the figure.

TABLE I

"OP-1" Refers generically to the group of morphogenically active proteins expressed from part or all of a DNA sequence encoding OP-1 protein, including allelic and species variants thereof, e.g., human OP-1 ("hOP-1"), or mouse OP-1 ("mOP-1".) The cDNA sequences and the amino acids encoding the full length proteins are provided in Seq. Id Nos. 1 and 2 (hOP1) and Seq. ID Nos. 3 and 4 (mOP1.) The mature proteins are defined by residues 293–431 (hOP1) and 292–430 (mOP1), wherein the conserved seven cysteine skeleton is defined by residues 330–431 and 329–430, respectively, and the N-terminal extensions are defined by residues 293–329 and 292–329, respectively. The "pro" regions of the proteins, cleaved to yield the mature, morphogenically active proteins, are defined essentially by residues 30–292 (hOP1) and residues 30–291 (mOP1).

"OP-2" refers generically to the group of active proteins expressed from part or all of a DNA sequence encoding OP-2 protein, including allelic and species variants thereof, e.g., human OP-2 ("hOP-2") or mouse OP-2 ("mOP-2".) The full length proteins are provided in Seq. ID Nos. 5 and 6 (hOP2) and Seq. ID Nos. 7 and 8 (mOP2.) The mature proteins are defined essentially by residues 264–402 (hOP2) and 261–399 (mOP2), wherein the conserved seven cysteine skeleton is defined by residues 301–402 and 298–399, respectively, and the N-terminal extensions are defined by residues 264–300 and 261–297, respectively. The "pro" regions of the proteins, cleaved to yield the mature, morphogenically active proteins likely are defined essentially by residues 18–263 (hOP2) and residues 18–260 (mOP2). (Another cleavage site also occurs 21 residues upstream for both OP-2 proteins.)

"OP-3" refers generically to the group of active proteins expressed from part or all of a DNA sequence encoding OP-3 protein, including allelic and species variants thereof, e.g., mouse OP-3 ("mOP-3".) The full length protein is provided in Seq. ID No. 9. The mature protein is defined essentially by residues 261–399 or 264–399, wherein the conserved seven cysteine skeleton is defined by residues 298–399 and the N-terminal extension is defined by residues 264–297 or 261–297. The "pro" region of the protein, cleaved to yield the mature, morphogenically active proteins likely is defined essentially by residues 20–262.

"BMP2/BMP4" refers to protein sequences encoded by the human BMP2 and BMP4 genes. The amino acid sequence for the full length proteins, referred to in the literature as BMP2A and BMP2B, or BMP2 and BMP4, appear in Seq. ID Nos. 10 and 11, respectively, and in Wozney, et al. (1988) Science 242:1528–1534. The pro domain for BMP2 (BMP2A) likely includes residues 25–248 or 25–282; the mature protein, residues 249–396 or 283–396, of which residues 249–296/283–296 define the N-terminal extension and 295–396 define the C-terminal domain. The pro domain for BMP4 (BMP2B) likely includes residues 25–256 or 25–292; the mature protein, residues 257–408 or 293–408, of which 257–307/293–307 define the N-terminal extension, and 308–408 define the C-terminal domain.

"DPP" refers to protein sequences encoded by the Drosophila DPP gene. The amino acid sequence for the full length protein, including the mature form and the pro region, appears in Seq. ID No. 12 and in Padgett, et al (1987) Nature 325: 81–84. The pro domain likely extends from the signal peptide cleavage site to residue 456; the mature protein likely is defined by residues 457–588, where residues 457–586 define the N-terminal extension and 487–588 define the C-terminal domain.

"Vgl" refers to protein sequences encoded by the Xenopus Vgl gene. The amino acid sequence for the full length protein, including the mature form and the pro region, appears in Seq.ID No. 13 and in Weeks (1987) Cell 51: 861–867. The pro domain likely extends from the signal peptide cleavage site to residue 246; the mature protein likely is defined by residues 247–360, where residues 247–258 define the N-terminal extension, and residues 259–360 define the C-terminal domain.

"Vgr-1" refers to protein sequences encoded by the murine Vgr-1 gene. The amino acid sequence for the full length protein, including the mature form and the pro region, appears in Seq. ID No. 14 and in Lyons, et al, (1989) PNAS 86: 4554–4558. The pro domain likely extends from the signal peptide cleavage site to residue 299; the mature protein likely is defined by residues 300–438, where residues 300–336 define the N-terminal extension and residues 337–438 define the C-terminus.

"GDF-1" refers to protein sequences encoded by the human GDF-1 gene. The cDNA and encoded amino sequence for the full length protein is provided in Seq. ID. No. 15 and Lee (1991) PNAS 88:4250–4254. The pro domain likely extends from the signal peptide cleavage site to residue 214; the mature protein likely is defined by residues 215–372, where residues 215–256 define the N-terminal extension and residues 257–372 define the C-terminus.

"60A" refers to protein sequences encoded by the Drosophila 60A gene. The amino acid sequence for the full length protein appears in Seq. ID No. 16 and in Wharton et al. (1991) PNAS 88:9214–9218) The pro domain likely extends from the signal peptide cleavage site to residue 324; the mature protein likely is defined by residues 325–455, wherein residues 325–353 define the N-terminal extension and residues 354–455 define the C-terminus.

"BMP3" refers to protein sequences encoded by the human BMP3 gene. The amino acid sequence for the full length protein, including the mature form and the pro region, appears in Seq.ID No. 17 and in Wozney et al. (1988) Science 242: 1528–1534. The pro domain likely extends from the signal peptide cleavage site to residue 290; the mature protein likely is defined by residues 291–472, wherein residues 291–370 define the N-terminal extension and residues 371–472 define the C-terminus.

"BMP5" refers to protein sequences encoded by the human BMP5 gene. The amino acid sequence for the full length protein, including the mature form and the pro region, appears in Seq.ID No. 18 and in Celeste, et al. (1990) PNAS 87: 9843–9847. The pro domain likely extends from the signal peptide cleavage site to residue 316; the mature protein likely is defined by residues 317–454, where residues 317–352 define the N-terminus and residues 352–454 define the C-terminus.

"BMP6" refers to protein sequences encoded by the human BMP6 gene. The amino acid sequence for the full length protein, including the mature form and the pro region, appears in Seq. ID No. 19 and in Celeste, et al. (1990) *PNAS* 87: 9843–5847. The pro domain likely includes extends from the signal peptide cleavage site to residue 374; the mature sequence likely includes residues 375–513, where residues 375–411 define the N-terminus and residues 412–513 define the C-terminus.

Note that the OP-2 and OP-3 proteins have an additional cysteine residue in the C-terminal region (e.g., see residue (341 in SEQ ID NO: 5), in addition to the conserved cysteine skeleton in common with the other proteins in this family. The GDF-1 protein has a four amino acid insert within the conserved skeleton ("Gly-Gly-Pro-Pro") but this insert likely does not interfere with the relationship of the cysteines in the folded structure. In addition, the CBMP2 proteins are missing one amino acid residue within the cysteine skeleton.

The dimeric morphogen species are inactive when reduced, but are active as oxidized homodimers and when oxidized in combination with other morphogens of this invention. Thus, as defined herein, a morphogen useful in a soluble morphogen complex is a dimeric protein comprising a pair of polypeptide chains, wherein each polypeptide chain has less than 200 amino acids and comprises at least the C-terminal six, preferably seven cysteine skeleton defined by residues 335–431 of Seq. ID No. 1, including functionally equivalent arrangements of these cysteines (e.g., amino acid insertions or deletions which alter the linear arrangement of the cysteines in the sequence but not their relationship in the folded structure), such that, when the polypeptide chains are folded, the dimeric protein species comprising the pair of polypeptide chains has the appropriate three-dimensional structure, including the appropriate intra- or inter-chain disulfide bonds such that the protein is capable of acting as a morphogen as defined herein. The solubility of these structures is improved when the mature dimeric form of a morphogen, in accordance with the invention, is complexed with at least one, and preferably two, pro domains.

Various generic sequences (Generic Sequence 1–6) defining preferred C-terminal sequences useful in the soluble morphogens of this invention are described in U.S. Ser. No. 07/923,780, now abandoned in favor of continuation application U.S. Ser. No. 08/432,883, incorporated herein above by reference. Two currently preferred generic sequences are described below.

Generic Sequence 7 (Seq. ID No. 20) and Generic Sequence 8 (Seq. ID No. 21) disclosed below, accommodate the homologies shared among preferred morphogen protein family members identified to date, including OP-1, OP-2, OP-3, CBMP2A, CBMP2B, BMP3, 60A, DPP, Vgl, BMP5, BMP6, Vrg-1, and GDF-1. The amino acid sequences for these proteins are described herein (see Sequence Listing) and/or in the art, as well as in PCT publication U.S. Ser. No. 92/07358 (WO93/04692), filed Aug. 28, 1992, for example. The generic sequences include both the amino acid identity shared by these sequences in the C-terminal domain, defined by the six and seven cysteine skeletons (Generic Sequences 7 and 8, respectively), as well as alternative residues for the variable positions within the sequence. The generic sequences allow for an additional cysteine at position 41 (Generic Sequence 7) or position 46 (Generic Sequence 8), providing an appropriate cysteine skeleton where inter- or intramolecular disulfide bonds can form, and containing certain critical amino acids which influence the tertiary structure of the proteins.

```
               Generic Sequence 7

Leu Xaa Xaa Xaa Phe
     1               5

Xaa Xaa Xaa Gly Trp Xaa Xaa Xaa Xaa
                10

Xaa Xaa Pro Xaa Xaa Xaa Xaa Ala
    15                  20

Xaa Tyr Cys Xaa Gly Xaa Cys Xaa
        25                  30

Xaa Pro Xaa Xaa Xaa Xaa Xaa
                35

Xaa Xaa Xaa Asn His Ala Xaa Xaa
            40              45

Xaa Xaa Xaa Xaa Xaa Xaa Xaa
                50

Xaa Xaa Xaa Xaa Xaa Xaa Xaa Cys
    55                      60

Cys Xaa Pro Xaa Xaa Xaa Xaa Xaa
                65

Xaa Xaa Xaa Leu Xaa Xaa Xaa
    70              75

Xaa Xaa Xaa Xaa Val Xaa Leu Xaa
                80

Xaa Xaa Xaa Xaa Met Xaa Val Xaa
    85                  90

Xaa Cys Xaa Cys Xaa
        95
``` wherein each Xaa is independently selected from a group of one or more specified amino acids defined as follows: "Res." means "residue" and Xaa at res.2=(Tyr or Lys); Xaa at res.3=Val or Ile); Xaa at res.4=(Ser, Asp or Glu); Xaa at res.6=(Arg, Gln, Ser, Lys or Ala); Xaa at res.7=(Asp or Glu); Xaa at res.8=(Leu, Val or Ile); Xaa at res.11=(Gln, Leu, Asp, His, Asn or Ser); Xaa at res.12=(Asp, Arg, Asn or Glu); Xaa at res. 13=(Trp or Ser); Xaa at res.14=(Ile or Val); Xaa at res.15=(Ile or Val); Xaa at res.16 (Ala or Ser); Xaa at res.18=(Glu, Gln, Leu, Lys, Pro or Arg); Xaa at res.19=(Gly or Ser); Xaa at res.20=(Tyr or Phe); Xaa at res.21=(Ala, Ser, Asp, Met, His, Gln, Leu or Gly); Xaa at res.23=(Tyr, Asn or Phe); Xaa at res.26=(Glu, His, Tyr, Asp, Gln, Ala or Ser); Xaa at res.28=(Glu, Lys, Asp, Gln or Ala); Xaa at res.30= (Ala, Ser, Pro, Gln, Ile or Asn); Xaa at res.31=(Phe, Leu or Tyr); Xaa at res.33=(Leu, Val or Met); Xaa at res.34=(Asn, Asp, Ala, Thr or Pro); Xaa at res.35=(Ser, Asp, Glu, Leu, Ala or Lys); Xaa at res.36=(Tyr, Cys, His, Ser or Ile); Xaa at res.37=(Met, Phe, Gly or Leu); Xaa at res.38=(Asn, Ser or Lys); Xaa at res.39=(Ala, Ser, Gly or Pro); Xaa at res.40= (Thr, Leu or Ser); Xaa at res.44=(Ile, Val or Thr); Xaa at res.45=(Val, Leu, Met or Ile); Xaa at res.46=(Gln or Arg); Xaa at res.47=(Thr, Ala or Ser); Xaa at res.48=(Leu or Ile); Xaa at res.49=(Val or Met); Xaa at res.50=(His, Asn or Arg); Xaa at res.51=(Phe, Leu, Asn, Ser, Ala or Val); Xaa at res.52=(Ile, Met, Asn, Ala, Val, Gly or Leu); Xaa at res.53= (Asn, Lys, Ala, Glu, Gly or Phe); Xaa at res.54=(Pro, Ser or Val); Xaa at res.55=(Glu, Asp, Asn, Gly, Val, Pro or Lys); Xaa at res.56=(Thr, Ala, Val, Lys, Asp, Tyr, Ser, Gly, Ile or His); Xaa at res.57=(Val, Ala or Ile); Xaa at res.58=(Pro or Asp); Xaa at res.59=(Lys, Leu or Glu); Xaa at res.60=(Pro, Val or Ala); Xaa at res.63=(Ala or Val); Xaa at res.65=(Thr, Ala or Glu); Xaa at res.66=(Gln, Lys, Arg or Glu); Xaa at res.67=(Leu, Met or Val); Xaa at res.68=(Asn, Ser, Asp or Gly); Xaa at res.69=(Ala, Pro or Ser); Xaa at res.70=(Ile, Thr, Val or Leu); Xaa at res.71=(Ser, Ala or Pro); Xaa at res.72=(Val, Leu, Met or Ile); Xaa at res.74=(Tyr or Phe); Xaa at res.75=(Phe, Tyr, Leu or His); Xaa at res.76=(Asp, Asn or Leu); Xaa at res.77=(Asp, Glu, Asn, Arg or Ser); Xaa at res.78=(Ser, Gln, Asn, Tyr or Asp); Xaa at res.79=(Ser, Asn, Asp, Glu or Lys); Xaa at res.80=(Asn, Thr or Lys); Xaa at res.82=(Ile, Val or Asn); Xaa at res.84=(Lys or Arg); Xaa at res.85=(Lys, Asn, Gln, His, Arg or Val); Xaa at res.86=(Tyr, Glu or His); Xaa at res.87=(Arg, Gln, Glu or Pro); Xaa at res.88=(Asn, Glu, Trp or Asp); Xaa at res.90=(Val, Thr, Ala or Ile); Xaa at res.92=(Arg, Lys, Val, Asp, Gln or Glu); Xaa at res.93=(Ala, Gly, Glu or Ser); Xaa at res.95=(Gly or Ala) and Xaa at res.97=(His or Arg).

As described above, Generic Sequence 8 (Seq. ID No. 21) includes all of Generic Sequence 7 and in addition includes the following sequence at its N-terminus:

```
Cys Xaa Xaa Xaa Xaa
 1               5
```

Accordingly, beginning with residue 7, each "Xaa" in Generic Seq. 8 is a specified amino acid defined as for Generic Seq. 7, with the distinction that each residue number described for Generic Sequence 7 is shifted by five in Generic Seq. 8. Thus, "Xaa at res.2=(Tyr or Lys)" in Gen. Seq. 7 refers to Xaa at res. 7 in Generic Seq. 8. In Generic Seq. 8, Xaa at res.2=(Lys, Arg, Ala or Gln); Xaa at res.3=(Lys, Arg or Met); Xaa at res.4=(His, Arg or Gln); and Xaa at res.5=(Glu, Ser, His, Gly, Arg, Pro, Thr, or Tyr).

Accordingly, other useful sequences defining preferred C-terminal sequences are those sharing at least 70% amino acid sequence homology or "similarity", and preferably 80% homology or similarity with any of the sequences incorporated into Generic Seq. 7 and 8 above. These are anticipated to include allelic, species other sequence amino acid sequence variants, as well as novel members of this morphogenic family of proteins. As used herein, "amino acid sequence homology" is understood to mean amino acid sequence similarity, and homologous sequences share identical or similar amino acids, where similar amino acids are conserved amino acids as defined by Dayoff et al., *Atlas of Protein Sequence and Structure*; vol.5, Suppl.3, pp.345–362 (M. O. Dayoff, ed., Nat'l BioMed. Research Fdn., Washington D.C. 1978.) Thus, a candidate sequence sharing 70% amino acid homology with a reference sequence requires that, following alignment of the candidate sequence with the reference sequence, 70% of the amino acids in the candidate sequence are identical to the corresponding amino acid sequences in the reference sequence, or constitute a conserved amino acid change thereto. "Amino acid sequence identity" is understood to require identical amino acids between two aligned sequences. Thus, a candidate sequence sharing 60% amino acid identity with a reference sequence requires that, following alignment of the candidate sequence with the reference sequence, 60% of the amino acids in the candidate sequence are identical to the corresponding amino acid in the reference sequence.

As used herein, all homologies and identities calculated use OP-1 as the reference sequence. Also as used herein, sequences are aligned for homology and identity calculations using the method of Needleman et al. (1970) *J. Mol. Biol.* 48:443–453 and identities calculated by the Align program (DNAstar, Inc.) In all cases, internal gaps and amino acid insertions in the candidate sequence as aligned are ignored when making the homology/identity calculation.

Also as used herein, "sequence variant" is understood to mean an amino acid variant form of the morphogen protein, wherein the amino acid change or changes in the sequence do not alter significantly the morphogenic activity (e.g., tissue regeneration activity). of the protein, and the variant molecule performs substantially the same function in substantially the same way as the naturally occurring form of the molecule. Sequence variants may include single or multiple amino acid changes, and are intended to include chimeric sequences as described below. The variants may be naturally occurring or may be biosynthetically induced by using standard recombinant DNA techniques or chemical protein synthesis methodologies.

The currently most preferred protein sequences useful in soluble morphogen complexes in this invention include those having greater than 60% identity, preferably greater than 65% identity, with the amino acid sequence defining the conserved six cysteine skeleton of hOP1 (e.g., residues 335–431 of Seq. ID No. 1). These most preferred sequences include both allelic and species variants of the OP-1 and OP-2 proteins, including the Drosophila 60A protein. Accordingly, in another preferred aspect of the invention, useful morphogens include active proteins comprising species of polypeptide chains having the generic amino acid sequence herein referred to as "OPX", which accommodates the homologies between the various identified species of OP1 and OP2 (Seq. ID No. 22).

Useful N-terminal extension sequences are listed in FIG. 2 for use with the C-terminal domains described above. Also as described above, the full length N-terminal extensions, or truncated forms thereof, may be used in preferred dimeric species. The mature dimeric species may be produced from intact DNAs, or truncated forms thereof. It also is envisioned as an embodiment of the invention that chimeric morphogen sequences can be used. Thus, DNAs encoding chimeric morphogens may be constructed using part or all of N-terminal extension from one morphogen and a C-terminal domain derived from one or more other morphogens. These chimeric proteins may be synthesized using standard recombinant DNA methodology and/or automated chemical nucleic acid synthesis methodology well described in the art. Other chimeric morphogens include soluble morphogen complexes where the pro domain is encoded from a DNA sequence corresponding to one morphogen, and part or all of the mature domain is encoded by DNA derived from other, different morphogen(s). These soluble chimerics may be produced from a single synthetic DNA as described below, or, alternatively, may be formulated in vitro from isolated components also as described herein below.

Finally, the morphogen pro domains and/or mature form N-terminal extensions themselves may be useful as tissue targeting sequences. As described above, the morphogen family members share significant sequence homology in their C-terminal active domains. By contrast, the sequences diverge significantly in the sequences which define the pro domain and the N-terminal 39 amino acids of the mature protein. Accordingly, the pro domain and/or N-terminal extension sequence may be morphogen-specific. Accordingly, part or all of these morphogen-specific sequences may serve as tissue targeting sequences for the morphogens described herein. For example, the N-terminal extension and/or pro domains may interact specifically with one or more molecules at the target tissue to direct the morphogen associated with the pro domain to that tissue. Thus, for example, the morphogen-specific sequences of OP-1, BMP2 or BMP4, all of which proteins are found naturally associated with bone tissue (see, for example, U.S. Pat. No. 5,011,691) may be particularly useful sequences when the morphogen complex is to be targeted to bone. Similarly, BMP6 (or Vgr-1) specific sequences may be used when targeting to lung tissue is desired. Alternatively, the morphogen-specific sequences of GDF-1 may be used to target soluble morphogen complexes to nerve tissue, particularly brain tissue, where GDF-1 appears to be primarily expressed (see, for example, U.S. Ser. No. 922,813 now abandoned in favor of continuation application U.S. Ser. No. 08/260,675, and Lee, PNAS, 88:4250–4254 (1991), incorporated herein by reference).

II. Recombinant Production of Soluble Morphogen Complexes

Soluble morphogen complexes can be produced from eukaryotic host cells, preferably mammalian cells, using standard recombinant expression techniques. An exemplary protocol currently preferred, is provided below, using a particular vector construct and chinese hamster ovary (CHO) cell line. Those skilled in the art will appreciate that other expression systems are contemplated to be useful, including other vectors and other cell systems, and the invention is not intended to be limited to soluble morphogenic protein complexes produced only by the method detailed hereinbelow. Similar results to those described herein have been observed using recombinant expression systems developed for COS and BSC cells.

Morphogen DNA encoding the precursor sequence is subcloned into an insertion site of a suitable, commercially available pUC-type vector (e.g., pUC-19, ATCC #37254, Rockville, Md.), along with a suitable promoter/enhancer sequences and 3' termination sequences. Useful DNA sequences include the published sequences encoding these proteins, and/or synthetic constructs. Currently preferred promoter/enhancer sequences are the CMV promoter (human cytomegalovirus major intermediate—early promoter) and the mouse mammary tumor virus promoter (mMTV) boosted by the rous sarcoma virus LTR enhancer sequence (e.g., from Clontech, Inc., Palo Alto). Expression also may be further enhanced using transactivating enhancer sequences. The plasmid also contains DHFR as an amplifiable marker, under SV40 early promoter control (ATCC #37148). Transfection, cell culturing, gene amplification and protein expression conditions are standard conditions, well known in the art, such as are described, for example in Ausubel et al., ed., Current Protocols in Molecular Biology, John Wiley & Sons, NY (1989). Briefly, transfected cells are cultured in medium containing 0.1–0.5% dialyzed fetal calf serum (FCS) and stably transfected high expression cell lines are obtained by subcloning and evaluated by standard Western or Northern blot. Southern blots also are used to assess the state of integrated sequences and the extent of their copy number amplification.

A currently preferred expression vector contains the DHFR gene, under SV40 early promoter control, as both a selection marker and as an inducible gene amplifier. The DNA sequence for DHFR is well characterized in the art, and is available commercially. For example, a suitable vector may be generated from pMAM-neo (Clontech, Inc., Palo Alto, Calif.) by replacing the neo gene (BamHI digest) with an SphI-BamHI, or a PvuII-BamHI fragment from pSV5-DHFR (ATCC #37148), which contains the DHFR gene under SV40 early promoter control. A BamHI site can be engineered at the SphI or PvuII site using standard techniques (e.g., by linker insertion or site-directed mutagenesis) to allow insertion of the fragment into the vector backbone. The morphogen DNA can be inserted into the polylinker site downstream of the MMTV-LTR sequence (mouse mammary tumor virus LTR). The CMV promoter sequence then may be inserted into the expression vector (e.g., from pCDM8, Invitrogen, Inc.) The SV40 early promoter, which drives DHFR expression, preferably is modified in these vectors to reduce the level of DHFR mRNA produced.

The currently preferred mammalian cell line is a CHO Chinese hamster ovary, cell line, and the preferred procedure for establishing a stable morphogen production cell line with high expression levels comprises transfecting a stable CHO cell line, preferably CHO-DXB11, with the expression vector described above, isolating clones with high morphogen expression levels, and subjecting these clones to cycles of subcloning using a limited dilution method described below to obtain a population of high expression clones. Subcloning preferably is performed in the absence of MTX to identify stable high expression clones which do not require addition of MTX to the growth media for morphogen production.

In the subcloning protocol cells are seeded on ten 100 mm petri dishes at a cell density of either 50 or 100 cells per plate, with or preferably without MTX in the culture media. After 14 days of growth, clones are isolated using cloning cylinders and standard procedures, and cultured in 24-well plates. Clones then are screened for morphogen expression by Western immunoblots using standard procedures, and morphogen expression levels compared to parental lines. Cell line stability of high expression subclones then is determined by monitoring morphogen expression levels over multiple cell passages (e.g., four or five passages).

III. Isolation of Soluble Morphogen Complex from Conditioned Media or Body Fluid Morphogens are expressed from mammalian cells as soluble complexes. Typically, however the complex is disassociated during purification, generally by exposure to denaturants often added to the purification solutions, such as detergents, alcohols, organic solvents, chaotropic agents and compounds added to reduce the pH of the solution. Provided below is a currently preferred protocol for purifying the soluble proteins from conditioned media (or, optionally, a body fluid such as serum, cerebro-spinal or peritoneal fluid), under non-denaturing conditions. The method is rapid, reproducible and yields isolated soluble morphogen complexes in substantially pure form.

Soluble morphogen complexes can be isolated from conditioned media using a simple, three step chromatographic protocol performed in the absence of denaturants. The protocol involves running the media (or body fluid) over an affinity column, followed by ion exchange and gel filtration chromatographies. The affinity column described below is a Zn-IMAC column. The present protocol has general applicability to the purification of a variety of morphogens, all of which are anticipated to be isolatable using only minor modifications of the protocol described below. An alternative protocol also envisioned to have utility an immunoaffinity column, created using standard procedures and, for example, using antibody specific for a given morphogen pro domain (complexed, for example, to a protein A-conjugated Sepharose column.) Protocols for developing immunoaffinity columns are well described in the art, (see, for example, Guide to Protein Purification, M. Deutscher, ed., Academic Press, San Diego, 1990, particularly sections VII and XI.)

In this experiment OP-1 was expressed in CHO cells as described above. The CHO cell conditioned media containing 0.5% FBS was initially purified using Immobilized Metal-Ion Affinity Chromatography (IMAC). The soluble OP-1 complex from conditioned media binds very selectively to the Zn-IMAC resin and a high concentration of imidazole (50 mM imidazole, pH 8.0) is required for the effective elution of the bound complex. The Zn-IMAC step separates the soluble OP-1 from the bulk of the contaminating serum proteins that elute in the flow through and 35 mM imidazole wash fractions. The Zn-IMAC purified soluble OP-1 is next applied to an S-Sepharose cation-exchange column equilibrated in 20 mM NaPO$_4$ (pH 7.0) with 50 mM NaCl. This S-Sepharose step serves to further purify and concentrate the soluble OP-1 complex in preparation for the following gel filtration step. The protein was applied to a Sephacryl S-200HR column equilibrated in TBS. Using substantially the same protocol, soluble morphogens also may be isolated from one or more body fluids, including serum, cerebro-spinal fluid or peritoneal fluid.

IMAC was performed using Chelating-Sepharose (Pharmacia) that had been charged with three column volumes of 0.2 M ZnSO$_4$. The conditioned media was titrated to pH 7.0 and applied directly to the ZN-IMAC resin equilibrated in 20 mM HEPES (pH 7.0) with 500 mM NaCl. The Zn-IMAC resin was loaded with 80 mL of starting conditioned media per mL of resin. After loading the column was washed with equilibration buffer and most of the contaminating proteins were eluted with 35 mM imidazole (pH 7.0) in equilibration buffer. The soluble OP-1 complex is then eluted with 50 mM imidazole (pH 8.0) in 20 mM HEPES and 500 mM NaCl.

The 50 mM imidazole eluate containing the soluble OP-1 complex was diluted with nine volumes of 20 mM NaPO$_4$ (pH 7.0) and applied to an S-Sepharose (Pharmacia) column equilibrated in 20 mM NaPO$_4$ (pH 7.0) with 50 mM NaCl. The S-Sepharose resin was loaded with an equivalent of 800 mL of starting conditioned media per mL of resin. After loading the S-Sepharose column was washed with equilibration buffer and eluted with 100 mM NaCl followed by 300 mM and 500 mM NaCl in 20 mM NaPO$_4$ (pH 7.0). The 300 mM NaCl pool was further purified using gel filtration chromatography. Fifty mls of the 300 mm NaCl eluate was applied to a 5.0×90 cm Sephacryl S-200HR (Pharmacia) equilibrated in Tris buffered saline (TBS), 50 mM Tris, 150 mM NaCl (pH 7.4). The column was eluted at a flow rate of 5 mL/minute collecting 10 mL fractions. The apparent molecular of the soluble OP-1 was determined by comparison to protein molecular weight standards (alcohol dehydrogenase (ADH, 150 kDa), bovine serum albumin (BSA, 68 kDa), carbonic anhydrase (CA, 30 kDa) and cytochrome C (cyt C, 12.5 kDa). (see FIG. 3) The purity of the S-200 column fractions was determined by separation on standard 15% polyacrylamide SDS gels stained with coomassie blue. The identity of the mature OP-1 and the pro-domain was determined by N-terminal sequence analysis after separation of the mature OP-1 from the pro-domain using standard reverse phase C18 HPLC.

Figure 3:
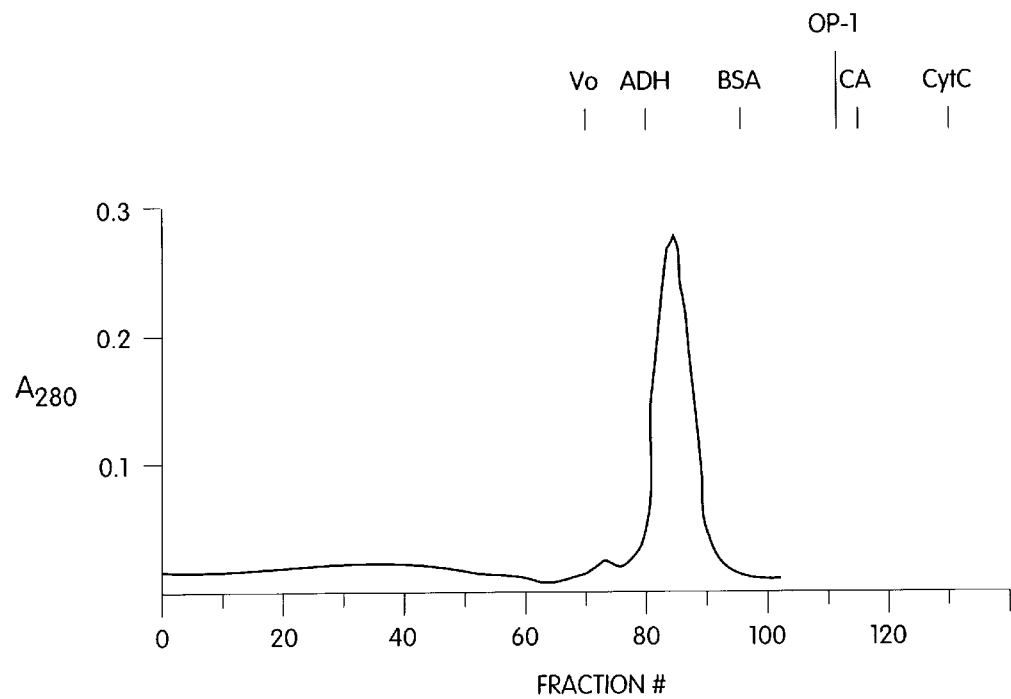
FIG. 3 is a gel filtration column elution profile of a soluble morphogen (OP-1) produced and purified from a mammalian cell culture by IMAC, S-Sepharose and S-200HR chromatography in TBS (Tris-buffered saline), wherein $V_o$ is the void volume, ADH is alcohol dehydrogenase (MW 150 kDa), BSA is bovine serum albumin (MW 67 kDa), CA is carbonic anhydrase (MW 29 kDa) and CytC is cytochrome C (MW 12.5 kDa).

FIG. 3 shows the absorbance profile at 280 nm. The soluble OP-1 complex elutes with an apparent molecular weight of 110 kDa. This agrees well with the predicted composition of the soluble OP-1 complex with one mature OP-1 dimer (35–36 kDa) associated with two pro-domains (39 kDa each). Purity of the final complex can be verified by running the appropriate fraction in a reduced 15% polyacrylamide gel.

The complex components can be verified by running the complex-containing fraction from the S-200 or S-200HR columns over a reverse phase C18 HPLC column and eluting in an acetonitrile gradient (in 0.1% TFA), using standard procedures. The complex is dissociated by this step, and the pro domain and mature species elute as separate species. These separate species then can be subjected to N-terminal sequencing using standard procedures (see, for example, *Guide to Protein Purification*, M. Deutscher, ed., Academic Press, San Diego, 1990, particularly pp. 602–613), and the identity of the isolated 36 kD, 39 kDa proteins confirmed as mature morphogen and isolated, cleaved pro domain, respectively. N-terminal sequencing of the isolated pro domain from mammalian cell produced OP-1 revealed 2 forms of the pro region, the intact form (beginning at residue 30 of Seq. ID No. 1) and a truncated form, (beginning at residue 48 of Seq. ID No. 1.) N-terminal sequencing of the polypeptide subunit of the isolated mature species reveals a range of N-termini for the mature sequence, beginning at residues 293, 300, 313, 315, 316, and 318, of Seq. ID No. 1, all of which are active as demonstrated by the standard bone induction assay.

V. In Vitro Soluble Morphogen Complex Formation

As an alternative to purifying soluble complexes from culture media or a body fluid, soluble complexes may be formulated from purified pro domains and mature dimeric species. Successful complex formation apparently requires association of the components under denaturing conditions sufficient to relax the folded structure of these molecules, without affecting disulfide bonds. Preferably, the denaturing conditions mimic the environment of an intracellular vesicle sufficiently such that the cleaved pro domain has an opportunity to associate with the mature dimeric species under relaxed folding. conditions. The concentration of denaturant in the solution then is decreased in a controlled, preferably step-wise manner, so as to allow proper refolding of the dimer and pro regions while maintaining the association of the pro domain with the dimer. Useful denaturants include 4–6M urea or guanidine hydrochloride (GuHCl), in buffered solutions of pH 4–10, preferably pH 6–8. The soluble complex then is formed by controlled dialysis or dilution into a solution having a final denaturant concentration of less than 0.1–2M urea or GuHCl, preferably 1–2 M urea of GuHCl, which then preferably can be diluted into a physiological buffer. Protein purification/renaturing procedures and considerations are well described in the art, and details for developing a suitable renaturing protocol readily can be determined by one having ordinary skill in the art. One useful text one the subject is *Guide to Protein Purification*, M. Deutscher, ed., Academic Press, San Diego, 1990, particularly section V. Complex formation also may be aided by addition of one or more chaperone proteins.

VI. Stability of Soluble Morphogen Complexes

The stability of the highly purified soluble morphogen complex in a physiological buffer, e.g., tris-buffered saline (TBS) and phosphate-buffered saline (PBS), can be enhanced by any of a number of means. Currently preferred is by means of a pro region that comprises at least the first 18 amino acids of the pro sequence (e.g., residues 30–47 of Seq. ID NO. 1 for OP-1), and preferably is the full length pro region. Residues 30–47 show sequence homology to the N-terminal portion of other morphogens and are believed to have particular utility in enhancing complex stability for all morphogens. Other useful means for enhancing the stability of soluble morphogen complexes include three classes of additive. These additives include basic amino acids (e.g., L-arginine, lysine and betaine); nonionic detergents (e.g., Tween 80 or Nonidet P-120); and carrier proteins (e.g., serum albumin and casein). These additives include 1–100 mM, preferably 10–70 mM, including 50 mM, basic amino acid;, 0.01–1.0%, preferably 0.05–0.2%, including 0.1% (v/v) nonionic detergent;, and 0.01–1.0%, preferably 0.05–0.2%, including 0.1% (w/v) carrier protein.

VII. Activity of Soluble Morphogen Complex

Association of the pro domain with the mature dimeric species does not interfere with the morphogenic activity of the protein in vivo as demonstrated by different activity assays. Specifically, soluble OP-1 complex provided in a standard rat osteopenia model induces significant increase in bone growth and osteocalcin production (see Table II, below), in a mannor analogous to the results obtained using mature morphogen.

The assay is analogous to the osteoporosis model described in U.S. Ser. No. 923,780, now abandoned in favor of continuation application U.S. Ser. No. 08/432,883, but uses aged female rats rather than ovariectomized animals. Briefly, young or aged female rats (Charles River Labs, 115–145, and 335–460 g body weight, respectively) were dosed daily for 7 days by intravenous tail injection, with either 20 $\mu$g/Kg body weight soluble OP-1, or 100 $\mu$g/Kg body weight soluble OP-1. Control groups of young and aged female rats were dosed only with tris-buffered saline (TBS). Water and food were provided to all animals ad libitum. After 14 days, animals were sacrificed, and new bone growth measured by standard histometric procedures. Osteocalcin concentrations in serum also were measured. No detrimental effects of morphogen administration were detected as determined by changes in animal body or organ weight or by hematology profiles.

TABLE II

| No. Animals | Animal Group | Bone Area (B.Ar/T.Ar) | Osteocalcin (ng/ml) |
| --- | --- | --- | --- |
| 4 | Control | 5.50 ± 0.64 | 11.89 ± 4.20 |
| 5 | Aged female, 20 $\mu$g/Kg sol. OP-1 | 7.68 ± 0.63** | 22.24 ± 2.28** |
| 5 | Aged female, 100 $\mu$g/Kg sol. OP-1 | 9.82 ± 3.31* | 20.87 ± 6.14* |

*$P < 0.05$
**$P < 0.01$

Similar experiments performed using soluble OP-1 complex in the osteoporosis model described in U.S. Ser. No. 923,780, now abandoned in favor of continuation application U.S. Ser. No. 08/432,883 and incorporated hereinabove by reference using ovariectomized rats also show no detrimental effect using the complex form.

Both mature and soluble morphogen also can induce CAM (cell adhesion molecule) expression, as described in copending U.S. Ser. No. 07/922,8133, filed Jul. 31, 1992 now abandoned in favor of continuation application U.S. Ser. No. 08/260,675, the disclosure of which is incorporated hereinabove by reference.

Briefly, and as described therein, induction of N-CAM isoforms (N-CAM-180, N-CAM-140 and N-CAM-120) can be monitored by reaction with the commercially available antibody mAb H28.123 (Sigma Co., St. Louis) and standard Western blot analysis (see, for example, *Molecular Cloning, A Laboratory Manual*, Sambrook et al. eds. Cold Spring Harbor Press, New York, 1989, particularly Section 18). Incubation of a growing culture of transformed cells of neuronal origin, NG108-15 cels (ATCC, Rockville, Md.) with either mature morphogen dimers or soluble morphogen complexes (10–100 ng/ml, preferably at least 40 ng/ml) induces a redifferentiation of these cells back to a morphology characteristic of untransformed neurons, including specific induction and/or enhanced expression of all 3 N-CAM isoforms. In the experiment, cells were subcultured on poly-L-lysine coated 6-well plates and grown in chemically defined medium for 2 days before the experiment. Fresh aliquots of morphogen were added (2.5 $\mu$l) daily.

VIII. Antibody Production

Provided below are standard protocols for polycolonal and monoclonal antibody production. For antibodies which recognize the soluble complex only, preferably the isolated pro region is used as the antigen; where antibodies specific to the mature protein are desired, the antigen preferably comprises at least the C-terminal domain or the intact mature sequence.

Polyclonal antibody may be prepared as follows. Each rabbit is given a primary immunization of 100 ug/500 $\mu$l of antigen, in 0.1% SDS mixed with 500 $\mu$l Complete Freund's Adjuvant. The antigen is injected subcutaneously at multiple sites on the back and flanks of the animal. The rabbit is boosted after a month in the same manner using incomplete Freund's Adjuvant. Test bleeds are taken from the ear vein seven days later. Two additional boosts and test bleeds are performed at monthly intervals until antibody against the morphogen antigen is detected in the serum using an ELISA assay. Then, the rabbit is boosted monthly with 100 $\mu$g of antigen and bled (15 ml per bleed) at days seven and ten after boosting.

Monoclonal antibody specific for a given morphogen may be prepared as follows. A mouse is given two injections of the morphogen antigen. The protein or protein fragment preferably is recombinantly produced. The first injection contains 100 $\mu$g of antigen in complete Freund's adjuvant and is given subcutaneously. The second injection contains 50 $\mu$g of antigen in incomplete adjuvant and is given intraperitoneally. The mouse then receives a total of 230 $\mu$g of OP-3 in four intraperitoneal injections at various times over an eight month period. One week prior to fusion, the mouse is boosted intraperitoneally with antigen (e.g., 100 $\mu$g) and may be additionally boosted with a peptide fragment conjugated to bovine serum albumin with a suitable crosslinking agent. This boost can be repeated five days (IP), four days (IP), three days (IP) and one day (IV) prior to fusion. The mouse spleen cells then are fused to commercially available myeloma cells at a ratio of 1:1 using PEG 1500 (Boehringer Mannheim, Germany), and the fused cells plated and screened for mature or soluble morphogen-specific antibodies using the appropriate portion of the morphogen sequence as antigen. The cell fusion and monoclonal screening steps readily are performed according to standard procedures well described in standard texts widely available in the art.

Using these standard procedures, anti-pro domain antisera was prepared from rabbits using the isolated pro domain from OP-1 as the antigen, and monoclonal antibody ("mAb") to the mature domain was produced in mice, using an *E. coli*-produced truncated form of OP-1 as antigen.

Standard Western blot analysis performed under reducing conditions demonstrates that the anti-pro domain antisera ("anti-pro") is specific for the pro domain only, while the mAb to mature OP-1 ("anti-mature OP-1") is specific for the dimer subunits, that the two antibodies do not cross-react, and that the antibodies and can be used to distinguish between soluble and mature protein forms in a sample, e.g., of conditioned media or serum. A tabular representation of the Western blot results is in Table III below, where reactivity of mAb to mature OP-1 is indicated by "yy", and reactivity of the anti-pro antisera is indicated by "xx".

TABLE III

| Antibody | Purified Sol OP1 | Conditioned CHO Cell Media | Isolated Pro Domain | Purified Dimer Subunits |
|---|---|---|---|---|
| "anti-pro" | xx | xx | xx | |
| "anti-mature OP-1" | yy | yy | | yy |

IX. Immunoassays

The ability to detect morphogens in solution and to distinguish between soluble and mature dimeric morphogen forms provides a valuable tool for diagnostic assays, allowing one to monitor the level and type of morphogen free in the body, e.g., in serum and other body fluids.

For example, OP-1 is an intimate participant in normal bone growth and resorption. Thus, soluble OP-1 is expected to be detected at higher concentrations in individuals experiencing high bone turnover, such as children, and at substantially lower levels in individuals with abnormally low rates of bone turnover, such as patients with osteoporosis, osteosarcoma, Paget's disease and the like. Monitoring the level of OP-1, or other bone targeted morphogens such as BMP2 and BMP4, in serum thus provides a means for evaluating the status of bone tissue in an individual, as well as a means for monitoring the efficacy of a treatment to regenerate damaged or lost bone tissue. Similarly, monitoring the level of endogenous GDF-1, can provide diagnostic information on the health of nerve tissue, particularly brain tissue. Moreover, following this disclosure one can distinguish between the level of soluble and mature forms in solution.

A currently preferred detection means for evaluating the level of morphogen in a body fluid comprises an immunoassay utilizing an antibody or other suitable binding protein capable of reacting specifically with a morphogen and being detected as part of a complex with the morphogen. Immunoassays may be performed using standard techniques known in the art and antibodies raised against a morphogen and specific for that morphogen. Antibodies which recognize a morphogen protein form of interest may be generated as described herein and these antibodies then used to monitor endogenous levels of protein in a body fluid, such as serum, whole blood or peritoneal fluid. To monitor endogenous concentrations of soluble morphogen, the antibody chosen preferably has binding specificity for the soluble form e.g., has specificity for the pro domain. Such antibodies may be generated by using the pro domain or a portion thereof as the antigen, essentially as described herein. A suitable pro domain for use as an antigen may be obtained by isolating the soluble complex and then separating the noncovalently associated pro domain from the mature domain using standard procedures, e.g., by passing the complex over an HPLC column, as described above or by separation by gel electrophoresis. Alternatively, the pro form of the protein in its monomeric form may be used as the antigen and the candidate antibodies screened by Western blot or other standard immunoassay for those which recognize the pro domain of the soluble form of the protein of interest, but not the mature form, also as described above.

Monomeric pro forms can be obtained from cell lysates of CHO produced cells, or from prokaryotic expression of a DNA encoding the pro form, in for example, *E. coli*. The pro form, which has an apparent molecular weight of about 50 kDa in mammalian cells, can then be isolated by HPLC and/or by gel electrophoresis, as described above.

In order to detect and/or quantitate the amount of morphogenic protein present in a solution, an immunoassay may be performed to detect the morphogen using a polyclonal or monoclonal antibody specific for that protein. Here, soluble and mature forms of the morphogen also may be distinguished by using antibodies that discriminate between the two forms of the proteins as described above. Currently preferred assays include ELISAS and radioimmunassays, including standard competitor assays useful for quantitating the morphogen in a sample, where an unknown amount of sample morphogen is allowed to react with anti-morphogen antibody and this interaction is competed with a known amount of labeled antigen. The level of bound or free labeled antigen at equilibrium then is measured to quantitate the amount of unlabeled antigen in solution, the amount of sample antigen being proportional to the amount of free labeled antigen. Exemplary protocols for these assays are provided below. However, as will be appreciated by those skilled in the art, variations of these protocols, as well as other immunoassays, are well known in the literature and within the skill of the art. For example, in the ELISA protocol provided below, soluble OP-1 is identified in a sample using biotinylated anti-pro antiserum. Biotinylated antibodies can be visualized in a colormetric assay or in a chemiluminescent assay, as described below. Alternatively, the antibody can be radio-labeled with a suitable molecule, such as $^{125}$I. Still another protocol that may be used is a solid phase immunoassay, preferably using an affinity column with anti-morphogen antibody complexed to the matrix surface and over which a serum sample may be passed. A detailed description of useful immunoassays, including protocols and general considerations is provided in, for example, *Molecular Cloning: A Laboratory Manual*, Sambrook et al., eds. Cold Spring Harbor Press, New York, 1989, particularly Section 18.

For serum assays, the serum preferably first is partially purified to remove some of the excess, contaminating serum proteins, such as serum albumin. Preferably the serum is extracted by precipitation in ammonium sulfate (e.g., 45%) such that the complex is precipitated. Further purification can be achieved using purification strategies that take advantage of the differential solubility of soluble morphogen complex or mature morphogens relative to that of the other proteins present in serum. Further purification also can be achieved by chromatographic techniques well known in the art.

Soluble OP-1 may be detected using a polyclonal antibody specific for the OP-1 pro domain in an ELISA, as follows. 1 $\mu$g/100 $\mu$l of affinity-purified polyclonal rabbit IgG specific for OP-1-pro is added to each well of a 96-well plate and incubated at 37° C. for an hour. The wells are washed four times with 0.167M sodium borate buffer with 0.15 M NaCl (BSB), pH 8.2, containing 0.1% Tween 20. To minimize non-specific binding, the wells are blocked by filling completely with 1% bovine serum albumin (BSA) in BSB and incubating for 1 hour at 37° C. The wells are then washed four times with BSB containing 0.1% Tween 20. A 100 $\mu$l aliquot of an appropriate dilution of each of the test samples of cell culture supernatant or serum sample is added to each well in triplicate and incubated at 37° C. for 30 min. After incubation, 100 $\mu$l biotinylated rabbit anti-pro serum (stock solution is about 1 mg/ml and diluted 1:400 in BSB containing 1% BSA before use) is added to each well and incubated at 37° C. for 30 min. The wells are then washed four times with BSB containing 0.1% Tween 20. 100 $\mu$l strepavidin-alkaline (Southern Biotechnology Associates, Inc. Birmingham, Ala., diluted 1:2000 in BSB containing 0.1% Tween 20 before use) is added to each well and incubated at 37° C. for 30 min. The plates are washed four times with 0.5M Tris buffered Saline (TBS), pH 7.2. 50 µl substrate (ELISA Amplification System Kit, Life Technologies, Inc., Bethesda, Md.) is added to each well incubated at room temperature for 15 min. Then, 50 µl amplifier (from the same amplification system kit) is added and incubated for another 15 min at room temperature. The reaction is stopped by the addition of 50 µl 0.3 M sulphuric acid. The OD at 490 nm of the solution in each well is recorded. To quantitate the level of soluble OP-1 in the sample, a standard curve is performed in parallel with the test samples. In the standard curve, known increasing amounts of purified OP-1-pro is added. Alternatively, using, for example, Lumi-phos 530 (Analytical Luminescence Laboratories) as the substrate and detection at 300–650 nm in a standard luminometer, complexes can be detected by chemiluminescence, which typically provides a more sensitive assay than detection by means of a visible color change.

Morphogen (soluble or mature form) may be detected in a standard plated-based radioimmunoassay as follows. Empirically determined limiting levels of anti-morphogen antibody (e.g., anti-OP-1, typically 50–80 ng/well) are bound to wells of a PVC plate e.g., in 50 µl PBS phosphate buffered saline. After sufficient incubation to allow binding at room temperature, typically one hour, the plate is washed in a PBS/Tween 20 solution, ("washing buffer"), and 200 µl of block (3% BSA, 0.1 µ lysine in 1×BSB) is added to each well and allowed to incubate for 1 hour, after which the wells are washed again in washing buffer. 40 µl of a sample composed of serially diluted plasma (preferably partially purified as described above) or morphogen standard (e.g., OP-1) is added to wells in triplicate. Samples preferably are diluted in PTTH (15 mM $KH_2PO_4$, 8 mM $Na_2PO_4$, 27 mM KCl, 137 mM NaCl, 0.05% Tween 20, 1 mg/ml HSA, 0.05% $NaN_3$, pH 7.2). 10 µl of labelled competitor antigen, preferably 100,000–500,000 cpm/sample is added (e.g., $^{125}I$ OP-1, radiolabelled using standard procedures), and plates are incubated overnight at 4° C. Plates then are washed in washing buffer, and allowed to dry. Wells are cut apart and bound labelled OP-1 counted in a standard gamma counter. The quantities of bound labelled antigen (e.g., $^{125}I$ OP-1) measured in the presence and absence of sample then are compared, the difference being proportional to the amount of sample antigen (morphogen) present in the sample fluid.

As a corollary assay method, immunoassays may be developed to detect endogenous anti-morphogen antibodies, and to distinguish between such antibodies to soluble or mature forms. Endogenous anti-morphogen antibodies have been detected in serum, and their level is known to increase, for example, upon implanting of an osteogenic device in a mammal. Without being limited to a particular theory, these antibodies may play a role in modulating morphogen activity by modulating the level of available protein in serum. Assays that monitor the level of endogenous antibodies in blood or their body fluids thus can be used in diagnostic assays to evaluate the status of a tissue, as well as to provide a means for monitoring the efficacy of a therapy for tissue regeneration.

The currently preferred means for detecting endogenous anti-morphogen antibodies is by means of a standard Western blot. See, for example, *Molecular Cloning: A Laboratory Manual* Sambrook et al., eds., Cold Spring Harbor Press, New York, 1989, particularly pages 18.60–18.75, incorporated herein by reference, for a detailed description of these assays. Purified mature or soluble morphogen is electrophoresed on an SDS polyacrylamide gel under oxidized or reduced conditions designed to separate the proteins in solution, and the proteins then transferred to a polyvinylidene difluoride microporus membrane (0.45 µm pore sizes) using standard buffers and procedures. The filter then is incubated with the serum being tested (at various dilutions). Antibodies bound to either the pro domain or the mature morphogen domain are detected by means of an anti-human antibody protein, e.g., goat anti-human Ig. Titers of the antimorphogen antibodies can be determined by further dilution of the serum until no signal is detected.

X. Formulations and Methods for Administering Soluble Morphogens as Therapeutic Agents The soluble morphogens of this invention are particularly useful as therapeutic agents to regenerate diseased or damaged tissue in a mammal, particularly a human.

The soluble morphogen complexes may be used to particular advantage in regeneration of damaged or diseased lung, heart, liver, kidney, nerve or pancreas tissue, as well as in the transplantation and/or grafting of these tissues and bone marrow, skin, gastrointestinal mucosa, and other living tissues.

The soluble morphogen complexes described herein may be provided to an individual by any suitable means, preferably directly or systemically, e.g., parenterally or orally. Where the morphogen is to be provided directly (e.g., locally, as by injection, to a desired tissue site), or parenterally, such as by intravenous, subcutaneous, intramuscular, intraorbital, ophthalmic, intraventricular, intracranial, intracapsular, intraspinal, intracisternal, intraperitoneal, buccal, rectal, vaginal, intranasal or by aerosol administration, the soluble morphogen complex preferably comprises part of an aqueous solution. The solution is physiologically acceptable so that in addition to delivery of the desired morphogen to the patient, the solution does not otherwise adversely affect the patient's electrolyte and volume balance. The aqueous medium for the soluble morphogen thus may comprise normal physiologic saline (0.9% NaCl, 0.15M), pH 7–7.4.

Soluble morphogens of this invention are readily purified from cultured cell media into a physiological buffer, as described above. In addition, and as described above, if desired, the soluble complexes may be formulated with one or more additional additives, including basic amino acids (e.g., L-arginine, lysine, betaine); non-ionic detergents (e.g. Tween-80 or Nonidet-120) and carrier proteins (e.g., serum albumin and casein).

Useful solutions for oral or parenteral administration may be prepared by any of the methods well known in the pharmaceutical art, described, for example, in *Remington's Pharmaceutical Sciences*, (Gennaro, A., ed.), Mack Pub., 1990. Formulations may include, for example, polyalkylene glycols such as polyethylene glycol, oils of vegetable origin, hydrogenated naphthalenes, and the like. Formulations for direct administration, in particular, may include glycerol and other compositions of high viscosity. Biocompatible, preferably bioresorbable polymers, including, for example, hyaluronic acid, collagen, tricalcium phosphate, polybutyrate, polylactide, polyglycolide and lactide/glycolide copolymers, may be useful excipients to control the release of the soluble morphogen in vivo.

Other potentially useful parenteral delivery systems for these morphogens include ethylene-vinyl acetate copolymer particles, osmotic pumps, implantable infusion systems, and liposomes. Formulations for inhalation administration may contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally.

The soluble morphogens described herein also may be administered orally. Oral administration of proteins as therapeutics generally is not practiced as most proteins readily are degraded by digestive enzymes and acids in the mammalian digestive system before they can be absorbed into the bloodstream. However, the mature domains of the morphogens described herein typically are acid-stable and protease-resistant (see, for example, U.S. Pat. No. 4,968,590.) In addition, at least one morphogen, OP-1, has been identified, in mammary gland extract, colostrum and milk, as well as saliva. Moreover, the OP-1 purified from mammary gland extract is morphogenically active. For example, this protein induces endochondral bone formation in mammals when implanted subcutaneously in association with a suitable matrix material, using a standard in vivo bone assay, such as is disclosed in U.S. Pat. No. 4,968,590. In addition, endogenous morphogen also is detected in human serum (see above). Finally, comparative experiments with soluble and mature morphogens in a number of experiments defining morphogenic activity indicate that the non-covalent association of the pro domain with the dimeric species does not interfere with morphogenic activity. These findings indicate that oral and parenteral administration are viable means for administering morphogens to an individual, and that soluble morphogens have utility in systemic administration protocols.

The soluble complexes provided herein also may be associated with molecules capable of targeting the morphogen to a desired tissue. For example, tetracycline and diphosphonates (bisphosphonates) are known to bind to bone mineral, particularly at zones of bone remodeling, when they are provided systemically in a mammal. Accordingly, these molecules may be included as useful agents for targeting soluble morphogens to bone tissue. Alternatively, an antibody or other binding protein that interacts specifically with a surface molecule on the desired target tissue cells also may be used. Such targeting molecules further may be covalently associated to the morphogen complex, e.g., by chemical crosslinking, or by using standard genetic engineering means to create, for example, an acid labile bond such as an Asp-Pro linkage. Useful targeting molecules may be designed, for example, using the single chain binding site technology disclosed, for example, in U.S. Pat. No. 5,091,513.

Finally, the soluble morphogen complexes provided herein may be administered alone or in combination with other molecules known to have a beneficial effect on tissue morphogenesis, including molecules capable of tissue repair and regeneration and/or inhibiting inflammation. Examples of useful cofactors for stimulating bone tissue growth in osteoporotic individuals, for example, include but are not limited to, vitamin $D_3$, calcitonin, prostaglandins, parathyroid hormone, dexamethasone, estrogen and IGF-I or IGF-II. Useful cofactors for nerve tissue repair and regeneration may include nerve growth factors. Other useful cofactors include symptom-alleviating cofactors, including antiseptics, antibiotics, antiviral and antifungal agents and analgesics and anesthetics.

The compounds provided herein can be formulated into pharmaceutical compositions by admixture with pharmaceutically acceptable nontoxic excipients and carriers. As noted above, such compositions may be prepared for parenteral administration, particularly in the form of liquid solutions or suspensions; for oral administration, particularly in the form of tablets or capsules; or intranasally, particularly in the form of powders, nasal drops or aerosols. Where adhesion to a tissue surface is desired the composition may include the morphogen dispersed in a fibrinogen-thrombin composition or other bioadhesive such as is disclosed, for example in PCT US91/09275, the disclosure of which is incorporated herein by reference. The composition then may be painted, sprayed or otherwise applied to the desired tissue surface.

The compositions can be formulated for parenteral or oral administration to humans or other mammals in therapeutically effective amounts, e.g., amounts which provide appropriate concentrations of the morphogen to target tissue for a time sufficient to induce morphogenesis, including particular steps thereof, as described above.

Where the soluble morphogen complex is to be used as part of a transplant procedure, the morphogen may be provided to the living tissue or organ to be transplanted prior to removal of the tissue or organ from the donor. The morphogen may be provided to the donor host directly, as by injection of a formulation comprising the soluble complex into the tissue, or indirectly, e.g., by oral or parenteral administration, using any of the means described above.

Alternatively or, in addition, once removed from the donor, the organ or living tissue may be placed in a preservation solution containing the morphogen. In addition, the recipient also preferably is provided with the morphogen just prior to, or concommitant with, transplantation. In all cases, the soluble complex may be administered directly to the tissue at risk, as by injection to the tissue, or it may be provided systemically, either by oral or parenteral administration, using any of the methods and formulations described herein and/or known in the art.

Where the morphogen comprises part of a tissue or organ preservation solution, any commercially available preservation solution may be used to advantage. A useful preservation solution is described in U.S. Ser. No. 07/938,337 (WO93/04692), filed Aug. 28, 1992, and in PCT/US92/07358, both incorporated herein by reference.

As will be appreciated by those skilled in the art, the concentration of the compounds described in a therapeutic composition will vary depending upon a number of factors, including the dosage of the drug to be administered, the chemical characteristics (e.g., hydrophobicity) of the compounds employed, and the route of administration. The preferred dosage of drug to be administered also is likely to depend on such variables as the type and extent of tissue loss or defect, the overall health status of the particular patient, the relative biological efficacy of the compound selected, the formulation of the compound, the presence and types of excipients in the formulation, and the route of administration. In general terms, the compounds of this invention may be provided in an aqueous physiological buffer solution containing about 0.001 to 10% w/v compound for parenteral administration. Typical dose ranges are from about 10 ng/kg to about 1 g/kg of body weight per day; a preferred dose range is from about 0.1 µg/kg to 100 mg/kg of body weight. No obvious morphogen-induced pathological lesions are induced when mature morphogen (e.g., OP-1, 20 µg) is administered daily to normal growing rats for 21 consecutive days. Moreover, 10 µg systemic injections of morphogen (e.g., OP-1) injected daily for 10 days into normal newborn mice does not produce any gross abnormalities.

Where morphogens are administered systemically, in the methods of the present invention, preferably a large volume loading dose is used at the start of the treatment. The treatment then is continued with a maintenance dose. Further administration then can be determined by monitoring at intervals the levels of the morphogen in the blood.

OTHER EMBODIMENTS

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method for evaluating the disease state of a tissue or body fluid, comprising:

comparing in a tissue or body fluid sample a detected amount to an expected amount of an antibody capable of binding to a soluble morphogen complex, said complex comprising a dimeric protein having an amino acid sequence selected from the group consisting of:
(a) a sequence having at least 70% homology with the C-terminal seven-cysteine skeleton of human OP-1, residues 330–431 of SEQ. ID NO. 2, and
(b) Generic Sequence 7, SEQ. ID NO. 20;

said dimeric protein being in non-covalent association with a morphogen pro region or fragment thereof.

2. A method for evaluating the efficacy of a therapy for regenerating lost or damaged tissue in a mammal, the method comprising:

comparing in a tissue or body fluid sample a detected amount to an expected amount of an antibody capable of binding to a soluble morphogen complex, said complex comprising a dimeric protein having an amino acid sequence selected from the group consisting of:
(a) a sequence having at least 70% homology with the C-terminal seven-cysteine skeleton of human OP-1, residues 330–431 of SEQ. ID NO. 2, and
(b) Generic Sequence 7, SEQ. ID NO. 20;

said dimeric protein being in non-covalent association with a morphogen pro region or fragment thereof.

3. A method for diagnosing a tissue disorder in a mammal, the method comprising:

comparing in a tissue or body fluid sample a detected amount to an expected amount of an antibody capable of binding to a soluble morphogen complex, said complex comprising a dimeric protein having an amino acid sequence selected from the group consisting of:
(a) a sequence having at least 70% homology with the C-terminal seven-cysteine skeleton of human OP-1, residues 330–431 of SEQ. ID NO. 2, and
(b) Generic Sequence 7, SEQ. ID NO. 20;

said dimeric protein being in non-covalent association with a morphogen pro region or fragment thereof.

4. The method of claim 1 wherein said method is an immunoassay.

5. The method of claim 1, 2 or 3 wherein said pro region is derived from a bone morphogenic protein comprising at least 100 amino acids sharing at least 70% amino acid sequence homology with residues 330–431 of SEQ. ID NO. 2 (human OP-1).

6. The method of claim 1, 2 or 3 wherein said antibody is capable of distinguishing soluble morphogen complex from insoluble morphogen and non-morphogen proteins in a body fluid or tissue sample.

7. The method of claim 3 wherein said tissue disorder is a bone tissue disorder.

8. The method of claim 7 wherein said bone tissue disorder is selected from the group consisting of osteosarcoma, osteoporosis, and Paget's disease.

* * * * *

```
                            SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
        (A) LENGTH: 1822 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: HOMO SAPIENS
        (F) TISSUE TYPE: HIPPOCAMPUS (ix) FEATURE:
        (A) NAME/KEY: CDS
        (B) LOCATION: 49..1341
        (C) IDENTIFICATION METHOD: experimental
        (D) OTHER INFORMATION: /function= "OSTEOGENIC PROTEIN"
            /product= "OP1"
            /evidence= EXPERIMENTAL
            /standard_name= "OP1"

(xi) SEQUENCE DESCRIPTION: SEQ ID NO:1:

GGTGCGGGCC CGGAGCCCGG AGCCCGGGTA GCGCGTAGAG CCGGCGCG ATG CAC GTG        57
                                                    Met His Val
                                                     1

CGC TCA CTG CGA GCT GCG GCG CCG CAC AGC TTC GTG GCG CTC TGG GCA       105
Arg Ser Leu Arg Ala Ala Ala Pro His Ser Phe Val Ala Leu Trp Ala
  5              10                  15

CCC CTG TTC CTG CTG CGC TCC GCC CTG GCC GAC TTC AGC CTG GAC AAC       153
Pro Leu Phe Leu Leu Arg Ser Ala Leu Ala Asp Phe Ser Leu Asp Asn
 20                  25                  30                  35

GAG GTG CAC TCG AGC TTC ATC CAC CGG CGC CTC CGC AGC CAG GAG CGG       201
Glu Val His Ser Ser Phe Ile His Arg Arg Leu Arg Ser Gln Glu Arg
                 40                  45                  50

CGG GAG ATG CAG CGC GAG ATC CTC TCC ATT TTG GGC TTG CCC CAC CGC       249
Arg Glu Met Gln Arg Glu Ile Leu Ser Ile Leu Gly Leu Pro His Arg
             55                  60                  65

CCG CGC CCG CAC CTC CAG GGC AAG CAC AAC TCG GCA CCC ATG TTC ATG       297
Pro Arg Pro His Leu Gln Gly Lys His Asn Ser Ala Pro Met Phe Met
         70                  75                  80

CTG GAC CTG TAC AAC GCC ATG GCG GTG GAG GAG GGC GGC GGG CCC GGC       345
Leu Asp Leu Tyr Asn Ala Met Ala Val Glu Glu Gly Gly Gly Pro Gly
     85                  90                  95

GGC CAG GGC TTC TCC TAC CCC TAC AAG GCC GTC TTC AGT ACC CAG GGC       393
Gly Gln Gly Phe Ser Tyr Pro Tyr Lys Ala Val Phe Ser Thr Gln Gly
100                 105                 110                 115

CCC CCT CTG GCC AGC CTG CAA GAT AGC CAT TTC CTC ACC GAC GCC GAC       441
Pro Pro Leu Ala Ser Leu Gln Asp Ser His Phe Leu Thr Asp Ala Asp
```

```
                    120                 125                 130
ATG GTC ATG AGC TTC GTC AAC CTC GTG GAA CAT GAC AAG GAA TTC TTC       489
Met Val Met Ser Phe Val Asn Leu Val Glu His Asp Lys Glu Phe Phe
            135                 140                 145

CAC CCA CGC TAC CAC CAT CGA GAG TTC CGG TTT GAT CTT TCC AAG ATC       537
His Pro Arg Tyr His His Arg Glu Phe Arg Phe Asp Leu Ser Lys Ile
            150                 155                 160

CCA GAA GGG GAA GCT GTC ACG GCA GCC GAA TTC CGG ATC TAC AAG GAC       585
Pro Glu Gly Glu Ala Val Thr Ala Ala Glu Phe Arg Ile Tyr Lys Asp
            165                 170                 175

TAC ATC CGG GAA CGC TTC GAC AAT GAG ACG TTC CGG ATC AGC GTT TAT       633
Tyr Ile Arg Glu Arg Phe Asp Asn Glu Thr Phe Arg Ile Ser Val Tyr
180                 185                 190                 195

CAG GTG CTC CAG GAG CAC TTG GGC AGG GAA TCG GAT CTC TTC CTG CTC       681
Gln Val Leu Gln Glu His Leu Gly Arg Glu Ser Asp Leu Phe Leu Leu
            200                 205                 210

GAC AGC CGT ACC CTC TGG GCC TCG GAG GAG GGC TGG CTG GTG TTT GAC       729
Asp Ser Arg Thr Leu Trp Ala Ser Glu Glu Gly Trp Leu Val Phe Asp
            215                 220                 225

ATC ACA GCC ACC AGC AAC CAC TGG GTG GTC AAT CCG CGG CAC AAC CTG       777
Ile Thr Ala Thr Ser Asn His Trp Val Val Asn Pro Arg His Asn Leu
            230                 235                 240

GGC CTG CAG CTC TCG GTG GAG ACG CTG GAT GGG CAG AGC ATC AAC CCC       825
Gly Leu Gln Leu Ser Val Glu Thr Leu Asp Gly Gln Ser Ile Asn Pro
245                 250                 255

AAG TTG GCG GGC CTG ATT GGG CGG CAC GGG CCC CAG AAC AAG CAG CCC       873
Lys Leu Ala Gly Leu Ile Gly Arg His Gly Pro Gln Asn Lys Gln Pro
260                 265                 270                 275

TTC ATG GTG GCT TTC TTC AAG GCC ACG GAG GTC CAC TTC CGC AGC ATC       921
Phe Met Val Ala Phe Phe Lys Ala Thr Glu Val His Phe Arg Ser Ile
            280                 285                 290

CGG TCC ACG GGG AGC AAA CAG CGC AGC CAG AAC CGC TCC AAG ACG CCC       969
Arg Ser Thr Gly Ser Lys Gln Arg Ser Gln Asn Arg Ser Lys Thr Pro
            295                 300                 305

AAG AAC CAG GAA GCC CTG CGG ATG GCC AAC GTG GCA GAG AAC AGC AGC      1017
Lys Asn Gln Glu Ala Leu Arg Met Ala Asn Val Ala Glu Asn Ser Ser
            310                 315                 320

AGC GAC CAG AGG CAG GCC TGT AAG AAG CAC GAG CTG TAT GTC AGC TTC      1065
Ser Asp Gln Arg Gln Ala Cys Lys Lys His Glu Leu Tyr Val Ser Phe
            325                 330                 335

CGA GAC CTG GGC TGG CAG GAC TGG ATC ATC GCG CCT GAA GGC TAC GCC      1113
Arg Asp Leu Gly Trp Gln Asp Trp Ile Ile Ala Pro Glu Gly Tyr Ala
340                 345                 350                 355

GCC TAC TAC TGT GAG GGG GAG TGT GCC TTC CCT CTG AAC TCC TAC ATG      1161
Ala Tyr Tyr Cys Glu Gly Glu Cys Ala Phe Pro Leu Asn Ser Tyr Met
            360                 365                 370

AAC GCC ACC AAC CAC GCC ATC GTG CAG ACG CTG GTC CAC TTC ATC AAC      1209
Asn Ala Thr Asn His Ala Ile Val Gln Thr Leu Val His Phe Ile Asn
            375                 380                 385

CCG GAA ACG GTG CCC AAG CCC TGC TGT GCG CCC ACG CAG CTC AAT GCC      1257
Pro Glu Thr Val Pro Lys Pro Cys Cys Ala Pro Thr Gln Leu Asn Ala
            390                 395                 400

ATC TCC GTC CTC TAC TTC GAT GAC AGC TCC AAC GTC ATC CTG AAG AAA      1305
Ile Ser Val Leu Tyr Phe Asp Asp Ser Ser Asn Val Ile Leu Lys Lys
            405                 410                 415

TAC AGA AAC ATG GTG GTC CGG GCC TGT GGC TGC CAC TAGCTCCTCC           1351
Tyr Arg Asn Met Val Val Arg Ala Cys Gly Cys His
420                 425                 430

GAGAATTCAG ACCCTTTGGG GCCAAGTTTT TCTGGATCCT CCATTGCTCG CCTTGGCCAG    1411
```

```
GAACCAGCAG ACCAACTGCC TTTTGTGAGA CCTTCCCCTC CCTATCCCCA ACTTTAAAGG      1471

TGTGAGAGTA TTAGGAAACA TGAGCAGCAT ATGGCTTTTG ATCAGTTTTT CAGTGGCAGC      1531

ATCCAATGAA CAAGATCCTA CAAGCTGTGC AGGCAAAACC TAGCAGGAAA AAAAAACAAC      1591

GCATAAAGAA AAATGGCCGG GCCAGGTCAT TGGCTGGGAA GTCTCAGCCA TGCACGGACT      1651

CGTTTCCAGA GGTAATTATG AGCGCCTACC AGCCAGGCCA CCCAGCCGTG GGAGGAAGGG      1711

GGCGTGGCAA GGGGTGGGCA CATTGGTGTC TGTGCGAAAG GAAAATTGAC CCGGAAGTTC      1771

CTGTAATAAA TGTCACAATA AAACGAATGA ATGAAAAAAA AAAAAAAAA A               1822

(2) INFORMATION FOR SEQ ID NO:2:

(i) SEQUENCE CHARACTERISTICS:
        (A) LENGTH: 431 amino acids
        (B) TYPE: amino acid
        (D) TOPOLOGY: linear (ii) MOLECULE TYPE: protein (xi) SEQUENCE DESCRIPTION: SEQ ID NO:2:
```

Met His Val Arg Ser Leu Arg Ala Ala Pro His Ser Phe Val Ala
 1               5                  10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Arg Leu Arg Ser
            35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
    115                 120                 125

Asp Ala Asp Met Val Met Ser Phe Val Asn Leu Val Glu His Asp Lys
130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
    195                 200                 205

Phe Leu Leu Asp Ser Arg Thr Leu Trp Ala Ser Glu Glu Gly Trp Leu
210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe

```
                275                 280                 285
Arg Ser Ile Arg Ser Thr Gly Ser Lys Gln Arg Ser Gln Asn Arg Ser
    290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
                340                 345                 350

Gly Tyr Ala Ala Tyr Tyr Cys Glu Gly Glu Cys Ala Phe Pro Leu Asn
                355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
                420                 425                 430
```

(2) INFORMATION FOR SEQ ID NO:3:

(i) SEQUENCE CHARACTERISTICS:
        (A) LENGTH: 1873 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 104..1393
        (D) OTHER INFORMATION: /function= "OSTEOGENIC PROTEIN"
            /product= "MOP1"
            /note= "MOP1 CDNA"

(xi) SEQUENCE DESCRIPTION: SEQ ID NO:3:

```
CTGCAGCAAG TGACCTCGGG TCGTGGACCG CTGCCCTGCC CCCTCCGCTG CCACCTGGGG        60

CGGCGCGGGC CCGGTGCCCC GGATCGCGCG TAGAGCCGGC GCG ATG CAC GTG CGC        115
                                              Met His Val Arg
                                                1

TCG CTG CGC GCT GCG GCG CCA CAC AGC TTC GTG GCG CTC TGG GCG CCT        163
Ser Leu Arg Ala Ala Ala Pro His Ser Phe Val Ala Leu Trp Ala Pro
  5                  10                  15                  20

CTG TTC TTG CTG CGC TCC GCC CTG GCC GAT TTC AGC CTG GAC AAC GAG        211
Leu Phe Leu Leu Arg Ser Ala Leu Ala Asp Phe Ser Leu Asp Asn Glu
                 25                  30                  35

GTG CAC TCC AGC TTC ATC CAC CGG CGC CTC CGC AGC CAG GAG CGG CGG        259
Val His Ser Ser Phe Ile His Arg Arg Leu Arg Ser Gln Glu Arg Arg
             40                  45                  50

GAG ATG CAG CGG GAG ATC CTG TCC ATC TTA GGG TTG CCC CAT CGC CCG        307
Glu Met Gln Arg Glu Ile Leu Ser Ile Leu Gly Leu Pro His Arg Pro
         55                  60                  65

CGC CCG CAC CTC CAG GGA AAG CAT AAT TCG GCG CCC ATG TTC ATG TTG        355
Arg Pro His Leu Gln Gly Lys His Asn Ser Ala Pro Met Phe Met Leu
     70                  75                  80

GAC CTG TAC AAC GCC ATG GCG GTG GAG GAG AGC GGG CCG GAC GGA CAG        403
Asp Leu Tyr Asn Ala Met Ala Val Glu Glu Ser Gly Pro Asp Gly Gln
 85                  90                  95                 100
```

-continued

| | | |
|---|---|---|
| GGC TTC TCC TAC CCC TAC AAG GCC GTC TTC AGT ACC CAG GGC CCC CCT<br>Gly Phe Ser Tyr Pro Tyr Lys Ala Val Phe Ser Thr Gln Gly Pro Pro<br>              105                      110                        115 | 451 |
| TTA GCC AGC CTG CAG GAC AGC CAT TTC CTC ACT GAC GCC GAC ATG GTC<br>Leu Ala Ser Leu Gln Asp Ser His Phe Leu Thr Asp Ala Asp Met Val<br>              120                      125                        130 | 499 |
| ATG AGC TTC GTC AAC CTA GTG GAA CAT GAC AAA GAA TTC TTC CAC CCT<br>Met Ser Phe Val Asn Leu Val Glu His Asp Lys Glu Phe Phe His Pro<br>              135                      140                        145 | 547 |
| CGA TAC CAC CAT CGG GAG TTC CGG TTT GAT CTT TCC AAG ATC CCC GAG<br>Arg Tyr His His Arg Glu Phe Arg Phe Asp Leu Ser Lys Ile Pro Glu<br>            150                      155                        160 | 595 |
| GGC GAA CGG GTG ACC GCA GCC GAA TTC AGG ATC TAT AAG GAC TAC ATC<br>Gly Glu Arg Val Thr Ala Ala Glu Phe Arg Ile Tyr Lys Asp Tyr Ile<br>165                      170                      175                        180 | 643 |
| CGG GAG CGA TTT GAC AAC GAG ACC TTC CAG ATC ACA GTC TAT CAG GTG<br>Arg Glu Arg Phe Asp Asn Glu Thr Phe Gln Ile Thr Val Tyr Gln Val<br>                      185                      190                        195 | 691 |
| CTC CAG GAG CAC TCA GGC AGG GAG TCG GAC CTC TTC TTG CTG GAC AGC<br>Leu Gln Glu His Ser Gly Arg Glu Ser Asp Leu Phe Leu Leu Asp Ser<br>            200                      205                        210 | 739 |
| CGC ACC ATC TGG GCT TCT GAG GAG GGC TGG TTG GTG TTT GAT ATC ACA<br>Arg Thr Ile Trp Ala Ser Glu Glu Gly Trp Leu Val Phe Asp Ile Thr<br>              215                      220                        225 | 787 |
| GCC ACC AGC AAC CAC TGG GTG GTC AAC CCT CGG CAC AAC CTG GGC TTA<br>Ala Thr Ser Asn His Trp Val Val Asn Pro Arg His Asn Leu Gly Leu<br>230                      235                      240 | 835 |
| CAG CTC TCT GTG GAG ACC CTG GAT GGG CAG AGC ATC AAC CCC AAG TTG<br>Gln Leu Ser Val Glu Thr Leu Asp Gly Gln Ser Ile Asn Pro Lys Leu<br>245                      250                      255                        260 | 883 |
| GCA GGC CTG ATT GGA CGG CAT GGA CCC CAG AAC AAG CAA CCC TTC ATG<br>Ala Gly Leu Ile Gly Arg His Gly Pro Gln Asn Lys Gln Pro Phe Met<br>                      265                      270                        275 | 931 |
| GTG GCC TTC TTC AAG GCC ACG GAA GTC CAT CTC CGT AGT ATC CGG TCC<br>Val Ala Phe Phe Lys Ala Thr Glu Val His Leu Arg Ser Ile Arg Ser<br>              280                      285                        290 | 979 |
| ACG GGG GGC AAG CAG CGC AGC CAG AAT CGC TCC AAG ACG CCA AAG AAC<br>Thr Gly Gly Lys Gln Arg Ser Gln Asn Arg Ser Lys Thr Pro Lys Asn<br>            295                      300                      305 | 1027 |
| CAA GAG GCC CTG AGG ATG GCC AGT GTG GCA GAA AAC AGC AGC AGT GAC<br>Gln Glu Ala Leu Arg Met Ala Ser Val Ala Glu Asn Ser Ser Ser Asp<br>310                      315                      320 | 1075 |
| CAG AGG CAG GCC TGC AAG AAA CAT GAG CTG TAC GTC AGC TTC CGA GAC<br>Gln Arg Gln Ala Cys Lys Lys His Glu Leu Tyr Val Ser Phe Arg Asp<br>325                      330                      335                        340 | 1123 |
| CTT GGC TGG CAG GAC TGG ATC ATT GCA CCT GAA GGC TAT GCT GCC TAC<br>Leu Gly Trp Gln Asp Trp Ile Ile Ala Pro Glu Gly Tyr Ala Ala Tyr<br>                      345                      350                        355 | 1171 |
| TAC TGT GAG GGA GAG TGC GCC TTC CCT CTG AAC TCC TAC ATG AAC GCC<br>Tyr Cys Glu Gly Glu Cys Ala Phe Pro Leu Asn Ser Tyr Met Asn Ala<br>              360                      365                        370 | 1219 |
| ACC AAC CAC GCC ATC GTC CAG ACA CTG GTT CAC TTC ATC AAC CCA GAC<br>Thr Asn His Ala Ile Val Gln Thr Leu Val His Phe Ile Asn Pro Asp<br>            375                      380                      385 | 1267 |
| ACA GTA CCC AAG CCC TGC TGT GCG CCC ACC CAG CTC AAC GCC ATC TCT<br>Thr Val Pro Lys Pro Cys Cys Ala Pro Thr Gln Leu Asn Ala Ile Ser<br>390                      395                      400 | 1315 |
| GTC CTC TAC TTC GAC GAC AGC TCT AAT GTC ATC CTG AAG AAG TAC AGA<br>Val Leu Tyr Phe Asp Asp Ser Ser Asn Val Ile Leu Lys Lys Tyr Arg<br>405                      410                      415                        420 | 1363 |

```
AAC ATG GTG GTC CGG GCC TGT GGC TGC CAC TAGCTCTTCC TGAGACCCTG       1413
Asn Met Val Val Arg Ala Cys Gly Cys His
            425                 430

ACCTTTGCGG GGCCACACCT TTCCAAATCT TCGATGTCTC ACCATCTAAG TCTCTCACTG   1473

CCCACCTTGG CGAGGAGAAC AGACCAACCT CTCCTGAGCC TTCCCTCACC TCCCAACCGG   1533

AAGCATGTAA GGGTTCCAGA AACCTGAGCG TGCAGCAGCT GATGAGCGCC CTTTCCTTCT   1593

GGCACGTGAC GGACAAGATC CTACCAGCTA CCACAGCAAA CGCCTAAGAG CAGGAAAAAT   1653

GTCTGCCAGG AAAGTGTCCA GTGTCCACAT GGCCCCTGGC GCTCTGAGTC TTTGAGGAGT   1713

AATCGCAAGC CTCGTTCAGC TGCAGCAGAA GGAAGGGCTT AGCCAGGGTG GGCGCTGGCG   1773

TCTGTGTTGA AGGGAAACCA AGCAGAAGCC ACTGTAATGA TATGTCACAA TAAAACCCAT   1833

GAATGAAAAA AAAAAAAAAA AAAAAAAAAA AAAAGAATTC                        1873

(2) INFORMATION FOR SEQ ID NO:4:

(i) SEQUENCE CHARACTERISTICS:
        (A) LENGTH: 430 amino acids
        (B) TYPE: amino acid
        (D) TOPOLOGY: linear (ii) MOLECULE TYPE: protein (xi) SEQUENCE DESCRIPTION: SEQ ID NO:4:

Met His Val Arg Ser Leu Arg Ala Ala Pro His Ser Phe Val Ala
  1               5                  10                  15

Leu Trp Ala Pro Leu Phe Leu Leu Arg Ser Ala Leu Ala Asp Phe Ser
                20                  25                  30

Leu Asp Asn Glu Val His Ser Ser Phe Ile His Arg Leu Arg Ser
            35                  40                  45

Gln Glu Arg Arg Glu Met Gln Arg Glu Ile Leu Ser Ile Leu Gly Leu
        50                  55                  60

Pro His Arg Pro Arg Pro His Leu Gln Gly Lys His Asn Ser Ala Pro
 65                 70                  75                  80

Met Phe Met Leu Asp Leu Tyr Asn Ala Met Ala Val Glu Glu Ser Gly
                85                  90                  95

Pro Asp Gly Gln Gly Phe Ser Tyr Pro Tyr Lys Ala Val Phe Ser Thr
            100                 105                 110

Gln Gly Pro Pro Leu Ala Ser Leu Gln Asp Ser His Phe Leu Thr Asp
        115                 120                 125

Ala Asp Met Val Met Ser Phe Val Asn Leu Val Glu His Asp Lys Glu
    130                 135                 140

Phe Phe His Pro Arg Tyr His His Arg Glu Phe Arg Phe Asp Leu Ser
145                 150                 155                 160

Lys Ile Pro Glu Gly Glu Arg Val Thr Ala Ala Glu Phe Arg Ile Tyr
                165                 170                 175

Lys Asp Tyr Ile Arg Glu Arg Phe Asp Asn Glu Thr Phe Gln Ile Thr
            180                 185                 190

Val Tyr Gln Val Leu Gln Glu His Ser Gly Arg Glu Ser Asp Leu Phe
        195                 200                 205

Leu Leu Asp Ser Arg Thr Ile Trp Ala Ser Glu Glu Gly Trp Leu Val
    210                 215                 220

Phe Asp Ile Thr Ala Thr Ser Asn His Trp Val Val Asn Pro Arg His
225                 230                 235                 240

Asn Leu Gly Leu Gln Leu Ser Val Glu Thr Leu Asp Gly Gln Ser Ile
```

```
                   245                 250                 255
       Asn Pro Lys Leu Ala Gly Leu Ile Gly Arg His Gly Pro Gln Asn Lys
                       260                 265                 270

Gln Pro Phe Met Val Ala Phe Phe Lys Ala Thr Glu Val His Leu Arg
                       275                 280                 285

Ser Ile Arg Ser Thr Gly Gly Lys Gln Arg Ser Gln Asn Arg Ser Lys
                       290                 295                 300

Thr Pro Lys Asn Gln Glu Ala Leu Arg Met Ala Ser Val Ala Glu Asn
       305                 310                 315                 320

Ser Ser Ser Asp Gln Arg Gln Ala Cys Lys Lys His Glu Leu Tyr Val
                       325                 330                 335

Ser Phe Arg Asp Leu Gly Trp Gln Asp Trp Ile Ile Ala Pro Glu Gly
                       340                 345                 350

Tyr Ala Ala Tyr Tyr Cys Glu Gly Glu Cys Ala Phe Pro Leu Asn Ser
                       355                 360                 365

Tyr Met Asn Ala Thr Asn His Ala Ile Val Gln Thr Leu Val His Phe
                       370                 375                 380

Ile Asn Pro Asp Thr Val Pro Lys Pro Cys Cys Ala Pro Thr Gln Leu
       385                 390                 395                 400

Asn Ala Ile Ser Val Leu Tyr Phe Asp Asp Ser Ser Asn Val Ile Leu
                       405                 410                 415

Lys Lys Tyr Arg Asn Met Val Val Arg Ala Cys Gly Cys His
                       420                 425                 430

(2) INFORMATION FOR SEQ ID NO:5:

(i) SEQUENCE CHARACTERISTICS:
        (A) LENGTH: 1723 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens
        (F) TISSUE TYPE: HIPPOCAMPUS (ix) FEATURE:
        (A) NAME/KEY: CDS
        (B) LOCATION: 490..1696
        (D) OTHER INFORMATION: /function= "OSTEOGENIC PROTEIN"
            /product= "hOP2-PP"
            /note= "hOP2 (cDNA)"

(xi) SEQUENCE DESCRIPTION: SEQ ID NO:5:

GGCGCCGGCA GAGCAGGAGT GGCTGGAGGA GCTGTGGTTG GAGCAGGAGG TGGCACGGCA      60

GGGCTGGAGG GCTCCCTATG AGTGGCGGAG ACGGCCCAGG AGGCGCTGGA GCAACAGCTC     120

CCACACCGCA CCAAGCGGTG GCTGCAGGAG CTCGCCCATC GCCCCTGCGC TGCTCGGACC     180

GCGGCCACAG CCGGACTGGC GGGTACGGCG GCGACAGAGG CATTGGCCGA GAGTCCCAGT     240

CCGCAGAGTA GCCCCGGCCT CGAGGCGGTG GCGTCCCGGT CCTCTCCGTC CAGGAGCCAG     300

GACAGGTGTC GCGCGGCGGG GCTCCAGGGA CCGCGCCTGA GGCCGGCTGC CCGCCCGTCC     360

CGCCCCGCCC CGCCGCCCGC CGCCCGCCGA GCCCAGCCTC CTTGCCGTCG GGGCGTCCCC     420

AGGCCCTGGG TCGGCCGCGG AGCCGATGCG CGCCCGCTGA GCGCCCCAGC TGAGCGCCCC     480

CGGCCTGCC ATG ACC GCG CTC CCC GGC CCG CTC TGG CTC CTG GGC CTG        528
           Met Thr Ala Leu Pro Gly Pro Leu Trp Leu Leu Gly Leu
            1               5                  10
```

```
GCG CTA TGC GCG CTG GGC GGG GGC GGC CCC GGC CTG CGA CCC CCG CCC      576
Ala Leu Cys Ala Leu Gly Gly Gly Gly Pro Gly Leu Arg Pro Pro Pro
 15                  20                  25

GGC TGT CCC CAG CGA CGT CTG GGC GCG CGC GAG CGC CGG GAC GTG CAG      624
Gly Cys Pro Gln Arg Arg Leu Gly Ala Arg Glu Arg Arg Asp Val Gln
 30                  35                  40                  45

CGC GAG ATC CTG GCG GTG CTC GGG CTG CCT GGG CGG CCC CGG CCC CGC      672
Arg Glu Ile Leu Ala Val Leu Gly Leu Pro Gly Arg Pro Arg Pro Arg
                 50                  55                  60

GCG CCA CCC GCC GCC TCC CGG CTG CCC GCG TCC GCG CCG CTC TTC ATG      720
Ala Pro Pro Ala Ala Ser Arg Leu Pro Ala Ser Ala Pro Leu Phe Met
             65                  70                  75

CTG GAC CTG TAC CAC GCC ATG GCC GGC GAC GAC GAC GAG GAC GGC GCG      768
Leu Asp Leu Tyr His Ala Met Ala Gly Asp Asp Asp Glu Asp Gly Ala
         80                  85                  90

CCC GCG GAG CGG CGC CTG GGC CGC GCC GAC CTG GTC ATG AGC TTC GTT      816
Pro Ala Glu Arg Arg Leu Gly Arg Ala Asp Leu Val Met Ser Phe Val
     95                 100                 105

AAC ATG GTG GAG CGA GAC CGT GCC CTG GGC CAC CAG GAG CCC CAT TGG      864
Asn Met Val Glu Arg Asp Arg Ala Leu Gly His Gln Glu Pro His Trp
110                 115                 120                 125

AAG GAG TTC CGC TTT GAC CTG ACC CAG ATC CCG GCT GGG GAG GCG GTC      912
Lys Glu Phe Arg Phe Asp Leu Thr Gln Ile Pro Ala Gly Glu Ala Val
                130                 135                 140

ACA GCT GCG GAG TTC CGG ATT TAC AAG GTG CCC AGC ATC CAC CTG CTC      960
Thr Ala Ala Glu Phe Arg Ile Tyr Lys Val Pro Ser Ile His Leu Leu
            145                 150                 155

AAC AGG ACC CTC CAC GTC AGC ATG TTC CAG GTG GTC CAG GAG CAG TCC     1008
Asn Arg Thr Leu His Val Ser Met Phe Gln Val Val Gln Glu Gln Ser
        160                 165                 170

AAC AGG GAG TCT GAC TTG TTC TTT TTG GAT CTT CAG ACG CTC CGA GCT     1056
Asn Arg Glu Ser Asp Leu Phe Phe Leu Asp Leu Gln Thr Leu Arg Ala
175                 180                 185

GGA GAC GAG GGC TGG CTG GTG CTG GAT GTC ACA GCA GCC AGT GAC TGC     1104
Gly Asp Glu Gly Trp Leu Val Leu Asp Val Thr Ala Ala Ser Asp Cys
190                 195                 200                 205

TGG TTG CTG AAG CGT CAC AAG GAC CTG GGA CTC CGC CTC TAT GTG GAG     1152
Trp Leu Leu Lys Arg His Lys Asp Leu Gly Leu Arg Leu Tyr Val Glu
                210                 215                 220

ACT GAG GAC GGG CAC AGC GTG GAT CCT GGC CTG GCC GGC CTG CTG GGT     1200
Thr Glu Asp Gly His Ser Val Asp Pro Gly Leu Ala Gly Leu Leu Gly
            225                 230                 235

CAA CGG GCC CCA CGC TCC CAA CAG CCT TTC GTG GTC ACT TTC TTC AGG     1248
Gln Arg Ala Pro Arg Ser Gln Gln Pro Phe Val Val Thr Phe Phe Arg
        240                 245                 250

GCC AGT CCG AGT CCC ATC CGC ACC CCT CGG GCA GTG AGG CCA CTG AGG     1296
Ala Ser Pro Ser Pro Ile Arg Thr Pro Arg Ala Val Arg Pro Leu Arg
255                 260                 265

AGG AGG CAG CCG AAG AAA AGC AAC GAG CTG CCG CAG GCC AAC GAC TC      1344
Arg Arg Gln Pro Lys Lys Ser Asn Glu Leu Pro Gln Ala Asn Arg Leu
270                 275                 280                 285

CCA GGG ATC TTT GAT GAC GTC CAC GGC TCC CAC GGC CGG CAG GTC TGC     1392
Pro Gly Ile Phe Asp Asp Val His Gly Ser His Gly Arg Gln Val Cys
                290                 295                 300

CGT CGG CAC GAG CTC TAC GTC AGC TTC CAG GAC CTC GGC TGG CTG GAC     1440
Arg Arg His Glu Leu Tyr Val Ser Phe Gln Asp Leu Gly Trp Leu Asp
            305                 310                 315

TGG GTC ATC GCT CCC CAA GGC TAC TCG GCC TAT TAC TGT GAG GGG GAG     1488
Trp Val Ile Ala Pro Gln Gly Tyr Ser Ala Tyr Tyr Cys Glu Gly Glu
        320                 325                 330
```

```
TGC TCC TTC CCA CTG GAC TCC TGC ATG AAT GCC ACC AAC CAC GCC ATC     1536
Cys Ser Phe Pro Leu Asp Ser Cys Met Asn Ala Thr Asn His Ala Ile
        335                 340                 345

CTG CAG TCC CTG GTG CAC CTG ATG AAG CCA AAC GCA GTC CCC AAG GCG     1584
Leu Gln Ser Leu Val His Leu Met Lys Pro Asn Ala Val Pro Lys Ala
350                 355                 360                 365

TGC TGT GCA CCC ACC AAG CTG AGC GCC ACC TCT GTG CTC TAC TAT GAC     1632
Cys Cys Ala Pro Thr Lys Leu Ser Ala Thr Ser Val Leu Tyr Tyr Asp
                370                 375                 380

AGC AGC AAC AAC GTC ATC CTG CGC AAA GCC CGC AAC ATG GTG GTC AAG     1680
Ser Ser Asn Asn Val Ile Leu Arg Lys Ala Arg Asn Met Val Val Lys
            385                 390                 395

GCC TGC GGC TGC CAC T GAGTCAGCCC GCCCAGCCCT ACTGCAG                 1723
Ala Cys Gly Cys His
            400

(2) INFORMATION FOR SEQ ID NO:6:

(i) SEQUENCE CHARACTERISTICS:
        (A) LENGTH: 402 amino acids
        (B) TYPE: amino acid
        (D) TOPOLOGY: linear (ii) MOLECULE TYPE: protein (xi) SEQUENCE DESCRIPTION: SEQ ID NO:6:

Met Thr Ala Leu Pro Gly Pro Leu Trp Leu Gly Leu Ala Leu Cys
 1               5                  10                  15

Ala Leu Gly Gly Gly Pro Gly Leu Arg Pro Pro Gly Cys Pro
            20                  25                  30

Gln Arg Arg Leu Gly Ala Arg Glu Arg Asp Val Gln Arg Glu Ile
            35                  40                  45

Leu Ala Val Leu Gly Leu Pro Gly Arg Pro Arg Pro Arg Ala Pro Pro
50                  55                  60

Ala Ala Ser Arg Leu Pro Ala Ser Ala Pro Leu Phe Met Leu Asp Leu
65                  70                  75                  80

Tyr His Ala Met Ala Gly Asp Asp Asp Glu Asp Gly Ala Pro Ala Glu
                85                  90                  95

Arg Arg Leu Gly Arg Ala Asp Leu Val Met Ser Phe Val Asn Met Val
            100                 105                 110

Glu Arg Asp Arg Ala Leu Gly His Gln Glu Pro His Trp Lys Glu Phe
        115                 120                 125

Arg Phe Asp Leu Thr Gln Ile Pro Ala Gly Glu Ala Val Thr Ala Ala
    130                 135                 140

Glu Phe Arg Ile Tyr Lys Val Pro Ser Ile His Leu Leu Asn Arg Thr
145                 150                 155                 160

Leu His Val Ser Met Phe Gln Val Val Gln Glu Gln Ser Asn Arg Glu
                165                 170                 175

Ser Asp Leu Phe Phe Leu Asp Leu Gln Thr Leu Arg Ala Gly Asp Glu
            180                 185                 190

Gly Trp Leu Val Leu Asp Val Thr Ala Ala Ser Asp Cys Trp Leu Leu
        195                 200                 205

Lys Arg His Lys Asp Leu Gly Leu Arg Leu Tyr Val Glu Thr Glu Asp
    210                 215                 220

Gly His Ser Val Asp Pro Gly Leu Ala Gly Leu Leu Gly Gln Arg Ala
225                 230                 235                 240

Pro Arg Ser Gln Gln Pro Phe Val Val Thr Phe Phe Arg Ala Ser Pro
```

```
                    245                 250                 255
Ser Pro Ile Arg Thr Pro Arg Ala Val Arg Pro Leu Arg Arg Gln
                260                 265                 270

Pro Lys Lys Ser Asn Glu Leu Pro Gln Ala Asn Arg Leu Pro Gly Ile
            275                 280                 285

Phe Asp Asp Val His Gly Ser His Gly Arg Gln Val Cys Arg Arg His
        290                 295                 300

Glu Leu Tyr Val Ser Phe Gln Asp Leu Gly Trp Leu Asp Trp Val Ile
305                 310                 315                 320

Ala Pro Gln Gly Tyr Ser Ala Tyr Tyr Cys Glu Gly Glu Cys Ser Phe
                325                 330                 335

Pro Leu Asp Ser Cys Met Asn Ala Thr Asn His Ala Ile Leu Gln Ser
                340                 345                 350

Leu Val His Leu Met Lys Pro Asn Ala Val Pro Lys Ala Cys Cys Ala
                355                 360                 365

Pro Thr Lys Leu Ser Ala Thr Ser Val Leu Tyr Tyr Asp Ser Ser Asn
            370                 375                 380

Asn Val Ile Leu Arg Lys Ala Arg Asn Met Val Val Lys Ala Cys Gly
385                 390                 395                 400

Cys His (2) INFORMATION FOR SEQ ID NO:7:

(i) SEQUENCE CHARACTERISTICS:
        (A) LENGTH: 1926 base pairs
        (B) TYPE: nucleic acid
        (C) STRANDEDNESS: single
        (D) TOPOLOGY: linear (vi) ORIGINAL SOURCE:
         (A) ORGANISM: MURIDAE
         (F) TISSUE TYPE: EMBRYO (ix) FEATURE:
         (A) NAME/KEY: CDS
         (B) LOCATION: 93..1289
         (D) OTHER INFORMATION: /function= "OSTEOGENIC PROTEIN"
             /product= "mOP2-PP"
             /note= "mOP2 cDNA"

(xi) SEQUENCE DESCRIPTION: SEQ ID NO:7:

GCCAGGCACA GGTGCGCCGT CTGGTCCTCC CCGTCTGGCG TCAGCCGAGC CCGACCAGCT      60

ACCAGTGGAT GCGCGCCGGC TGAAAGTCCG AG ATG GCT ATG CGT CCC GGG CCA       113
                                    Met Ala Met Arg Pro Gly Pro
                                     1               5

CTC TGG CTA TTG GGC CTT GCT CTG TGC GCG CTG GGA GGC GGC CAC GGT       161
Leu Trp Leu Leu Gly Leu Ala Leu Cys Ala Leu Gly Gly Gly His Gly
        10                  15                  20

CCG CGT CCC CCG CAC ACC TGT CCC CAG CGT CGC CTG GGA GCG CGC GAG       209
Pro Arg Pro Pro His Thr Cys Pro Gln Arg Arg Leu Gly Ala Arg Glu
    25                  30                  35

CGC CGC GAC ATG CAG CGT GAA ATC CTG GCG GTG CTC GGG CTA CCG GGA       257
Arg Arg Asp Met Gln Arg Glu Ile Leu Ala Val Leu Gly Leu Pro Gly
40                  45                  50                  55

CGG CCC CGA CCC CGT GCA CAA CCC GCC GCT GCC CGG CAG CCA GCG TCC       305
Arg Pro Arg Pro Arg Ala Gln Pro Ala Ala Ala Arg Gln Pro Ala Ser
                60                  65                  70

GCG CCC CTC TTC ATG TTG GAC CTA TAC CAC GCC ATG ACC GAT GAC GAC       353
Ala Pro Leu Phe Met Leu Asp Leu Tyr His Ala Met Thr Asp Asp Asp
            75                  80                  85
```

```
GAC GGC GGG CCA CCA CAG GCT CAC TTA GGC CGT GCC GAC CTG GTC ATG      401
Asp Gly Gly Pro Pro Gln Ala His Leu Gly Arg Ala Asp Leu Val Met
         90              95              100

AGC TTC GTC AAC ATG GTG GAA CGC GAC CGT ACC CTG GGC TAC CAG GAG      449
Ser Phe Val Asn Met Val Glu Arg Asp Arg Thr Leu Gly Tyr Gln Glu
    105             110             115

CCA CAC TGG AAG GAA TTC CAC TTT GAC CTA ACC CAG ATC CCT GCT GGG      497
Pro His Trp Lys Glu Phe His Phe Asp Leu Thr Gln Ile Pro Ala Gly
120             125             130             135

GAG GCT GTC ACA GCT GCT GAG TTC CGG ATC TAC AAA GAA CCC AGC ACC      545
Glu Ala Val Thr Ala Ala Glu Phe Arg Ile Tyr Lys Glu Pro Ser Thr
        140             145             150

CAC CCG CTC AAC ACA ACC CTC CAC ATC AGC ATG TTC GAA GTG GTC CAA      593
His Pro Leu Asn Thr Thr Leu His Ile Ser Met Phe Glu Val Val Gln
        155             160             165

GAG CAC TCC AAC AGG GAG TCT GAC TTG TTC TTT TTG GAT CTT CAG ACG      641
Glu His Ser Asn Arg Glu Ser Asp Leu Phe Phe Leu Asp Leu Gln Thr
        170             175             180

CTC CGA TCT GGG GAC GAG GGC TGG CTG GTG CTG GAC ATC ACA GCA GCC      689
Leu Arg Ser Gly Asp Glu Gly Trp Leu Val Leu Asp Ile Thr Ala Ala
    185             190             195

AGT GAC CGA TGG CTG CTG AAC CAT CAC AAG GAC CTG GGA CTC CGC CTC      737
Ser Asp Arg Trp Leu Leu Asn His His Lys Asp Leu Gly Leu Arg Leu
200             205             210             215

TAT GTG GAA ACC GCG GAT GGG CAC AGC ATG GAT CCT GGC CTG GCT GGT      785
Tyr Val Glu Thr Ala Asp Gly His Ser Met Asp Pro Gly Leu Ala Gly
            220             225             230

CTG CTT GGA CGA CAA GCA CCA CGC TCC AGA CAG CCT TTC ATG GTA ACC      833
Leu Leu Gly Arg Gln Ala Pro Arg Ser Arg Gln Pro Phe Met Val Thr
        235             240             245

TTC TTC AGG GCC AGC CAG AGT CCT GTG CGG GCC CCT CGG GCA GCG AGA      881
Phe Phe Arg Ala Ser Gln Ser Pro Val Arg Ala Pro Arg Ala Ala Arg
        250             255             260

CCA CTG AAG AGG AGG CAG CCA AAG AAA ACG AAC GAG CTT CCG CAC CCC      929
Pro Leu Lys Arg Arg Gln Pro Lys Lys Thr Asn Glu Leu Pro His Pro
    265             270             275

AAC AAA CTC CCA GGG ATC TTT GAT GAT GGC CAC GGT TCC CGC GGC AGA      977
Asn Lys Leu Pro Gly Ile Phe Asp Asp Gly His Gly Ser Arg Gly Arg
280             285             290             295

GAG GTT TGC CGC AGG CAT GAG CTC TAC GTC AGC TTC CGT GAC CTT GGC     1025
Glu Val Cys Arg Arg His Glu Leu Tyr Val Ser Phe Arg Asp Leu Gly
            300             305             310

TGG CTG GAC TGG GTC ATC GCC CCC CAG GGC TAC TCT GCC TAT TAC TGT     1073
Trp Leu Asp Trp Val Ile Ala Pro Gln Gly Tyr Ser Ala Tyr Tyr Cys
        315             320             325

GAG GGG GAG TGT GCT TTC CCA CTG GAC TCC TGT ATG AAC GCC ACC AAC     1121
Glu Gly Glu Cys Ala Phe Pro Leu Asp Ser Cys Met Asn Ala Thr Asn
        330             335             340

CAT GCC ATC TTG CAG TCT CTG GTG CAC CTG ATG AAG CCA GAT GTT GTC     1169
His Ala Ile Leu Gln Ser Leu Val His Leu Met Lys Pro Asp Val Val
        345             350             355

CCC AAG GCA TGC TGT GCA CCC ACC AAA CTG AGT GCC ACC TCT GTG CTG     1217
Pro Lys Ala Cys Cys Ala Pro Thr Lys Leu Ser Ala Thr Ser Val Leu
360             365             370             375

TAC TAT GAC AGC AGC AAC AAT GTC ATC CTG CGT AAA CAC CGT AAC ATG     1265
Tyr Tyr Asp Ser Ser Asn Asn Val Ile Leu Arg Lys His Arg Asn Met
            380             385             390

GTG GTC AAG GCC TGT GGC TGC CAC TGAGGCCCCG CCCAGCATCC TGCTTCTACT    1319
Val Val Lys Ala Cys Gly Cys His
                395
```

-continued

```
ACCTTACCAT CTGGCCGGGC CCCTCTCCAG AGGCAGAAAC CCTTCTATGT TATCATAGCT    1379

CAGACAGGGG CAATGGGAGG CCCTTCACTT CCCCTGGCCA CTTCCTGCTA AAATTCTGGT    1439

CTTTCCCAGT TCCTCTGTCC TTCATGGGGT TTCGGGGCTA TCACCCCGCC CTCTCCATCC    1499

TCCTACCCCA AGCATAGACT GAATGCACAC AGCATCCCAG AGCTATGCTA ACTGAGAGGT    1559

CTGGGGTCAG CACTGAAGGC CCACATGAGG AAGACTGATC CTTGGCCATC CTCAGCCCAC    1619

AATGGCAAAT TCTGGATGGT CTAAGAAGGC CCTGGAATTC TAAACTAGAT GATCTGGGCT    1679

CTCTGCACCA TTCATTGTGG CAGTTGGGAC ATTTTTAGGT ATAACAGACA CATACACTTA    1739

GATCAATGCA TCGCTGTACT CCTTGAAATC AGAGCTAGCT TGTTAGAAAA AGAATCAGAG    1799

CCAGGTATAG CGGTGCATGT CATTAATCCC AGCGCTAAAG AGACAGAGAC AGGAGAATCT    1859

CTGTGAGTTC AAGGCCACAT AGAAAGAGCC TGTCTCGGGA GCAGGAAAAA AAAAAAAAAC    1919

GGAATTC                                                              1926
```

(2) INFORMATION FOR SEQ ID NO:8:

(i) SEQUENCE CHARACTERISTICS:
        (A) LENGTH: 399 amino acids
        (B) TYPE: amino acid
        (D) TOPOLOGY: linear (ii) MOLECULE TYPE: protein (xi) SEQUENCE DESCRIPTION: SEQ ID NO:8:

```
Met Ala Met Arg Pro Gly Pro Leu Trp Leu Leu Gly Leu Ala Leu Cys
 1               5                  10                  15

Ala Leu Gly Gly Gly His Gly Pro Arg Pro Pro His Thr Cys Pro Gln
            20                  25                  30

Arg Arg Leu Gly Ala Arg Glu Arg Arg Asp Met Gln Arg Glu Ile Leu
        35                  40                  45

Ala Val Leu Gly Leu Pro Gly Arg Pro Arg Pro Arg Ala Gln Pro Ala
    50                  55                  60

Ala Ala Arg Gln Pro Ala Ser Ala Pro Leu Phe Met Leu Asp Leu Tyr
65                  70                  75                  80

His Ala Met Thr Asp Asp Asp Gly Gly Pro Pro Gln Ala His Leu
                85                  90                  95

Gly Arg Ala Asp Leu Val Met Ser Phe Val Asn Met Val Glu Arg Asp
            100                 105                 110

Arg Thr Leu Gly Tyr Gln Glu Pro His Trp Lys Glu Phe His Phe Asp
        115                 120                 125

Leu Thr Gln Ile Pro Ala Gly Glu Ala Val Thr Ala Ala Glu Phe Arg
    130                 135                 140

Ile Tyr Lys Glu Pro Ser Thr His Pro Leu Asn Thr Thr Leu His Ile
145                 150                 155                 160

Ser Met Phe Glu Val Val Gln Glu His Ser Asn Arg Glu Ser Asp Leu
                165                 170                 175

Phe Phe Leu Asp Leu Gln Thr Leu Arg Ser Gly Asp Glu Gly Trp Leu
            180                 185                 190

Val Leu Asp Ile Thr Ala Ala Ser Asp Arg Trp Leu Leu Asn His His
        195                 200                 205

Lys Asp Leu Gly Leu Arg Leu Tyr Val Glu Thr Ala Asp Gly His Ser
    210                 215                 220

Met Asp Pro Gly Leu Ala Gly Leu Leu Gly Arg Gln Ala Pro Arg Ser
225                 230                 235                 240
```

```
Arg Gln Pro Phe Met Val Thr Phe Phe Arg Ala Ser Gln Ser Pro Val
                245                 250                 255

Arg Ala Pro Arg Ala Ala Arg Pro Leu Lys Arg Arg Gln Pro Lys Lys
                260                 265                 270

Thr Asn Glu Leu Pro His Pro Asn Lys Leu Pro Gly Ile Phe Asp Asp
                275                 280                 285

Gly His Gly Ser Arg Gly Arg Glu Val Cys Arg Arg His Glu Leu Tyr
                290                 295                 300

Val Ser Phe Arg Asp Leu Gly Trp Leu Asp Trp Val Ile Ala Pro Gln
305                 310                 315                 320

Gly Tyr Ser Ala Tyr Tyr Cys Glu Gly Glu Cys Ala Phe Pro Leu Asp
                325                 330                 335

Ser Cys Met Asn Ala Thr Asn His Ala Ile Leu Gln Ser Leu Val His
                340                 345                 350

Leu Met Lys Pro Asp Val Val Pro Lys Ala Cys Cys Ala Pro Thr Lys
                355                 360                 365

Leu Ser Ala Thr Ser Val Leu Tyr Tyr Asp Ser Ser Asn Asn Val Ile
                370                 375                 380

Leu Arg Lys His Arg Asn Met Val Val Lys Ala Cys Gly Cys His
385                 390                 395

(2) INFORMATION FOR SEQ ID NO:9:

(i) SEQUENCE CHARACTERISTICS:
        (A) LENGTH: 399 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..399
        (D) OTHER INFORMATION: /note= "PRE-PRO-OP3 (MOUSE)"

(xi) SEQUENCE DESCRIPTION: SEQ ID NO:9:

Met Ala Ala Arg Pro Gly Leu Leu Trp Leu Leu Gly Leu Ala Leu Cys
1               5                   10                  15

Val Leu Gly Gly Gly His Leu Ser His Pro Pro His Val Phe Pro Gln
                20                  25                  30

Arg Arg Leu Gly Val Arg Glu Pro Arg Asp Met Gln Arg Glu Ile Arg
                35                  40                  45

Glu Val Leu Gly Leu Ala Gly Arg Pro Arg Ser Arg Ala Pro Val Gly
50                  55                  60

Ala Ala Gln Gln Pro Ala Ser Ala Pro Leu Phe Met Leu Asp Leu Tyr
65                  70                  75                  80

Arg Ala Met Thr Asp Asp Ser Gly Gly Thr Pro Gln Pro His Leu
                85                  90                  95

Asp Arg Ala Asp Leu Ile Met Ser Phe Val Asn Ile Val Glu Arg Asp
                100                 105                 110

Arg Thr Leu Gly Tyr Gln Glu Pro His Trp Lys Glu Phe His Phe Asp
                115                 120                 125

Leu Thr Gln Ile Pro Ala Gly Glu Ala Val Thr Ala Ala Glu Phe Arg
                130                 135                 140

Ile Tyr Lys Glu Pro Ser Thr His Pro Leu Asn Thr Thr Leu His Ile
145                 150                 155                 160
```

```
Ser Met Phe Glu Val Val Gln Glu His Ser Asn Arg Glu Ser Asp Leu
                165                 170                 175
Phe Phe Leu Asp Leu Gln Thr Leu Arg Ser Gly Asp Glu Gly Trp Leu
                180                 185                 190
Val Leu Asp Ile Thr Ala Ala Ser Asp Arg Trp Leu Leu Asn His His
                195                 200                 205
Lys Asp Leu Gly Leu Arg Leu Tyr Val Glu Thr Glu Asp Gly His Ser
210                 215                 220
Ile Asp Pro Gly Leu Ala Gly Leu Leu Gly Arg Gln Ala Pro Arg Ser
225                 230                 235                 240
Arg Gln Pro Phe Met Val Gly Phe Phe Arg Ala Asn Gln Ser Pro Val
                245                 250                 255
Arg Ala Pro Arg Thr Ala Arg Pro Leu Lys Lys Gln Leu Asn Gln
                260                 265                 270
Ile Asn Gln Leu Pro His Ser Asn Lys His Leu Gly Ile Leu Asp Asp
                275                 280                 285
Gly His Gly Ser His Gly Arg Glu Val Cys Arg Arg His Glu Leu Tyr
                290                 295                 300
Val Ser Phe Arg Asp Leu Gly Trp Leu Asp Ser Val Ile Ala Pro Gln
305                 310                 315                 320
Gly Tyr Ser Ala Tyr Tyr Cys Ala Gly Glu Cys Ile Tyr Pro Leu Asn
                325                 330                 335
Ser Cys Met Asn Ser Thr Asn His Ala Thr Met Gln Ala Leu Val His
                340                 345                 350
Leu Met Lys Pro Asp Ile Ile Pro Lys Val Cys Cys Val Pro Thr Glu
                355                 360                 365
Leu Ser Ala Ile Ser Leu Leu Tyr Tyr Asp Arg Asn Asn Val Ile
370                 375                 380
Leu Arg Arg Glu Arg Asn Met Val Val Gln Ala Cys Gly Cys His
385                 390                 395

(2) INFORMATION FOR SEQ ID NO:10:

(i) SEQUENCE CHARACTERISTICS:
        (A) LENGTH: 396 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..396
        (D) OTHER INFORMATION: /note= "PRE-PRO-BMP2 (HUMAN)"

(x) PUBLICATION INFORMATION:
        (A) AUTHORS: WOZNEY,
        (C) JOURNAL: SCIENCE
        (D) VOLUME: 242
        (F) PAGES: 1528-1534
        (G) DATE: 1988

(xi) SEQUENCE DESCRIPTION: SEQ ID NO:10:

Met Val Ala Gly Thr Arg Cys Leu Leu Ala Leu Leu Leu Pro Gln Val
1               5                   10                  15
Leu Leu Gly Gly Ala Ala Gly Leu Val Pro Glu Leu Gly Arg Arg Lys
                20                  25                  30
Phe Ala Ala Ala Ser Ser Gly Arg Pro Ser Ser Gln Pro Ser Asp Glu
                35                  40                  45
```

Val Leu Ser Glu Phe Glu Leu Arg Leu Leu Ser Met Phe Gly Leu Lys
 50                  55                  60

Gln Arg Pro Thr Pro Ser Arg Asp Ala Val Val Pro Pro Tyr Met Leu
 65                  70                  75                  80

Asp Leu Tyr Arg Arg His Ser Gly Gln Pro Gly Ser Pro Ala Pro Asp
                 85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
    130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
        355                 360                 365

Ile Ser Met Leu Tyr Leu Asp Glu Asn Glu Lys Val Val Leu Lys Asn
    370                 375                 380

Tyr Gln Asp Met Val Val Glu Gly Cys Gly Cys Arg
385                 390                 395

(2) INFORMATION FOR SEQ ID NO:11:

(i) SEQUENCE CHARACTERISTICS:
        (A) LENGTH: 408 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein (B) LOCATION: 1..408
(D) OTHER INFORMATION: /note= "PRE-PRO-BMP4 (HUMAN)"

(xi) SEQUENCE DESCRIPTION: SEQ ID NO:11:

| | | | | | | | | | | | | | | |
|---|---|---|---|---|---|---|---|---|---|---|---|---|---|---|
| Met | Ile | Pro | Gly | Asn | Arg | Met | Leu | Met | Val | Val | Leu | Leu | Cys | Gln | Val |
| 1 | | | | 5 | | | | | 10 | | | | | 15 | |

Leu Leu Gly Gly Ala Ser His Ala Ser Leu Ile Pro Glu Thr Gly Lys
            20                  25                  30

Lys Lys Val Ala Glu Ile Gln Gly His Ala Gly Gly Arg Arg Ser Gly
            35                  40                  45

Gln Ser His Glu Leu Leu Arg Asp Phe Glu Ala Thr Leu Leu Gln Met
        50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu Glu
                85                  90                  95

Glu Gln Ile His Ser Thr Gly Leu Glu Tyr Pro Glu Arg Pro Ala Ser
                100                 105                 110

Arg Ala Asn Thr Val Arg Ser Phe His His Glu Glu His Leu Glu Asn
            115                 120                 125

Ile Pro Gly Thr Ser Glu Asn Ser Ala Phe Arg Phe Leu Phe Asn Leu
130                 135                 140

Ser Ser Ile Pro Glu Asn Glu Val Ile Ser Ser Ala Glu Leu Arg Leu
145                 150                 155                 160

Phe Arg Glu Gln Val Asp Gln Gly Pro Asp Trp Glu Arg Gly Phe His
                165                 170                 175

Arg Ile Asn Ile Tyr Glu Val Met Lys Pro Pro Ala Glu Val Val Pro
            180                 185                 190

Gly His Leu Ile Thr Arg Leu Leu Asp Thr Arg Leu Val His His Asn
            195                 200                 205

Val Thr Arg Trp Glu Thr Phe Asp Val Ser Pro Ala Val Leu Arg Trp
210                 215                 220

Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
                245                 250                 255

Ser Leu Pro Gln Gly Ser Gly Asn Trp Ala Gln Leu Arg Pro Leu Leu
            260                 265                 270

Val Thr Phe Gly His Asp Gly Arg Gly His Ala Leu Thr Arg Arg Arg
            275                 280                 285

Arg Ala Lys Arg Ser Pro Lys His His Ser Gln Arg Ala Arg Lys Lys
290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335

Cys His Gly Asp Cys Pro Phe Pro Leu Ala Asp His Leu Asn Ser Thr
            340                 345                 350

Asn His Ala Ile Val Gln Thr Leu Val Asn Ser Val Asn Ser Ser Ile
            355                 360                 365

Pro Lys Ala Cys Cys Val Pro Thr Glu Leu Ser Ala Ile Ser Met Leu
370                 375                 380

Tyr Leu Asp Glu Tyr Asp Lys Val Val Leu Lys Asn Tyr Gln Glu Met
385                 390                 395                 400

```
Val Val Glu Gly Cys Gly Cys Arg
              405

(2) INFORMATION FOR SEQ ID NO:12:

(i) SEQUENCE CHARACTERISTICS:
        (A) LENGTH: 588 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..588
        (D) OTHER INFORMATION: /note= "PRE-PRO-DPP"

(x) PUBLICATION INFORMATION:
        (A) AUTHORS: PADGETT,
        (C) JOURNAL: NATURE
        (D) VOLUME: 325
        (F) PAGES: 81-84
        (G) DATE: 1987

(xi) SEQUENCE DESCRIPTION: SEQ ID NO:12:

Met Arg Ala Trp Leu Leu Leu Ala Val Leu Ala Thr Phe Gln Thr
 1               5                  10                  15

Ile Val Arg Val Ala Ser Thr Glu Asp Ile Ser Gln Arg Phe Ile Ala
                 20                  25                  30

Ala Ile Ala Pro Val Ala Ala His Ile Pro Leu Ala Ser Ala Ser Gly
                 35                  40                  45

Ser Gly Ser Gly Arg Ser Gly Ser Arg Ser Val Gly Ala Ser Thr Ser
 50                  55                      60

Thr Ala Leu Ala Lys Ala Phe Asn Pro Phe Ser Glu Pro Ala Ser Phe
 65                  70                  75                  80

Ser Asp Ser Asp Lys Ser His Arg Ser Lys Thr Asn Lys Lys Pro Ser
                 85                  90                  95

Lys Ser Asp Ala Asn Arg Gln Phe Asn Glu Val His Lys Pro Arg Thr
                100                 105                 110

Asp Gln Leu Glu Asn Ser Lys Asn Lys Ser Lys Gln Leu Val Asn Lys
                115                 120                 125

Pro Asn His Asn Lys Met Ala Val Lys Glu Gln Arg Ser His His Lys
130                 135                 140

Lys Ser His His His Arg Ser His Gln Pro Lys Gln Ala Ser Ala Ser
145                 150                 155                 160

Thr Glu Ser His Gln Ser Ser Ser Ile Glu Ser Ile Phe Val Glu Glu
                165                 170                 175

Pro Thr Leu Val Leu Asp Arg Glu Val Ala Ser Ile Asn Val Pro Ala
                180                 185                 190

Asn Ala Lys Ala Ile Ile Ala Glu Gln Gly Pro Ser Thr Tyr Ser Lys
                195                 200                 205

Glu Ala Leu Ile Lys Asp Lys Leu Lys Pro Asp Pro Ser Thr Leu Val
                210                 215                 220

Glu Ile Glu Lys Ser Leu Leu Ser Leu Phe Asn Met Lys Arg Pro Pro
225                 230                 235                 240

Lys Ile Asp Arg Ser Lys Ile Ile Pro Glu Pro Met Lys Lys Leu
                245                 250                 255

Tyr Ala Glu Ile Asn Gly His Glu Leu Asp Ser Val Asn Ile Pro Lys
                260                 265                 270
```

```
Pro Gly Leu Leu Thr Lys Ser Ala Asn Thr Val Arg Ser Phe Thr His
            275                 280                 285
Lys Asp Ser Lys Ile Asp Asp Arg Phe Pro His His His Arg Phe Arg
290                 295                 300
Leu His Phe Asp Val Lys Ser Ile Pro Ala Asp Glu Lys Leu Lys Ala
305                 310                 315                 320
Ala Glu Leu Gln Leu Thr Arg Asp Ala Leu Ser Gln Val Val Ala
                325                 330                 335
Ser Arg Ser Ser Ala Asn Arg Thr Arg Tyr Gln Val Leu Val Tyr Asp
            340                 345                 350
Ile Thr Arg Val Gly Val Arg Gly Gln Arg Glu Pro Ser Tyr Leu Leu
            355                 360                 365
Leu Asp Thr Lys Thr Val Arg Leu Asn Ser Thr Asp Thr Val Ser Leu
    370                 375                 380
Asp Val Gln Pro Ala Val Asp Arg Trp Leu Ala Ser Pro Gln Arg Asn
385                 390                 395                 400
Tyr Gly Leu Leu Val Glu Val Arg Thr Val Arg Ser Leu Lys Pro Ala
                405                 410                 415
Pro His His His Val Arg Leu Arg Arg Ser Ala Asp Glu Ala His Glu
                420                 425                 430
Arg Trp Gln His Lys Gln Pro Leu Leu Phe Thr Tyr Thr Asp Asp Gly
            435                 440                 445
Arg His Lys Ala Arg Ser Ile Arg Asp Val Ser Gly Gly Glu Gly Gly
            450                 455                 460
Gly Lys Gly Gly Arg Asn Lys Arg His Ala Arg Arg Pro Thr Arg Arg
465                 470                 475                 480
Lys Asn His Asp Asp Thr Cys Arg Arg His Ser Leu Tyr Val Asp Phe
                485                 490                 495
Ser Asp Val Gly Trp Asp Asp Trp Ile Val Ala Pro Leu Gly Tyr Asp
            500                 505                 510
Ala Tyr Tyr Cys His Gly Lys Cys Pro Phe Pro Leu Ala Asp His Phe
            515                 520                 525
Asn Ser Thr Asn His Ala Val Val Gln Thr Leu Val Asn Asn Met Asn
530                 535                 540
Pro Gly Lys Val Pro Lys Ala Cys Cys Val Pro Thr Gln Leu Asp Ser
545                 550                 555                 560
Val Ala Met Leu Tyr Leu Asn Asp Gln Ser Thr Val Val Leu Lys Asn
                565                 570                 575
Tyr Gln Glu Met Thr Val Val Gly Cys Gly Cys Arg
                580                 585
```

(2) INFORMATION FOR SEQ ID NO:13:

(i) SEQUENCE CHARACTERISTICS:
        (A) LENGTH: 360 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..360
        (D) OTHER INFORMATION: /note= "PRE-PRO-VG1"

(x) PUBLICATION INFORMATION:
        (A) AUTHORS: WEEKS, (C) JOURNAL: CELL
(D) VOLUME: 51
(F) PAGES: 861-867
(G) DATE: 1987

(xi) SEQUENCE DESCRIPTION: SEQ ID NO:13:

```
Met Val Trp Leu Arg Leu Trp Ala Phe Leu His Ile Leu Ala Ile Val
 1               5                  10                  15

Thr Leu Asp Pro Glu Leu Lys Arg Arg Glu Glu Leu Phe Leu Arg Ser
            20                  25                  30

Leu Gly Phe Ser Ser Lys Pro Asn Pro Val Ser Pro Pro Val Pro
        35                  40                  45

Ser Ile Leu Trp Arg Ile Phe Asn Gln Arg Met Gly Ser Ser Ile Gln
 50                  55                  60

Lys Lys Lys Pro Asp Leu Cys Phe Val Glu Glu Phe Asn Val Pro Gly
 65                  70                  75                  80

Ser Val Ile Arg Val Phe Pro Asp Gln Gly Arg Phe Ile Ile Pro Tyr
                85                  90                  95

Ser Asp Asp Ile His Pro Thr Gln Cys Leu Gly Lys Arg Leu Phe Phe
                100                 105                 110

Asn Ile Ser Ala Ile Glu Lys Glu Glu Arg Val Thr Met Gly Ser Gly
                115                 120                 125

Ile Glu Val Gln Pro Glu His Leu Leu Arg Lys Gly Ile Asp Leu Arg
 130                 135                 140

Leu Tyr Arg Thr Leu Gln Ile Thr Leu Lys Gly Met Gly Arg Ser Lys
 145                 150                 155                 160

Thr Ser Arg Lys Leu Leu Val Ala Gln Thr Phe Arg Leu Leu His Lys
                165                 170                 175

Ser Leu Phe Phe Asn Leu Thr Glu Ile Cys Gln Ser Trp Gln Asp Pro
                180                 185                 190

Leu Lys Asn Leu Gly Leu Val Leu Glu Ile Phe Pro Lys Lys Glu Ser
                195                 200                 205

Ser Trp Met Ser Thr Ala Asn Asp Glu Cys Lys Asp Ile Gln Thr Phe
 210                 215                 220

Leu Tyr Thr Ser Leu Leu Thr Val Thr Leu Asn Pro Leu Arg Cys Lys
 225                 230                 235                 240

Arg Pro Arg Arg Lys Arg Ser Tyr Ser Lys Leu Pro Phe Thr Ala Ser
                245                 250                 255

Asn Ile Cys Lys Lys Arg His Leu Tyr Val Glu Phe Lys Asp Val Gly
                260                 265                 270

Trp Gln Asn Trp Val Ile Ala Pro Gln Gly Tyr Met Ala Asn Tyr Cys
                275                 280                 285

Tyr Gly Glu Cys Pro Tyr Pro Leu Thr Glu Ile Leu Asn Gly Ser Asn
                290                 295                 300

His Ala Ile Leu Gln Thr Leu Val His Ser Ile Glu Pro Glu Asp Ile
 305                 310                 315                 320

Pro Leu Pro Cys Cys Val Pro Thr Lys Met Ser Pro Ile Ser Met Leu
                325                 330                 335

Phe Tyr Asp Asn Asn Asp Asn Val Val Leu Arg His Tyr Glu Asn Met
                340                 345                 350

Ala Val Asp Glu Cys Gly Cys Arg
                355                 360
```

(2) INFORMATION FOR SEQ ID NO:14:

```
    (i) SEQUENCE CHARACTERISTICS:
        (A) LENGTH: 438 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..438
        (D) OTHER INFORMATION: /note= "PRE-PRO-VGR1"

(x) PUBLICATION INFORMATION:
        (A) AUTHORS: LYONS,
        (C) JOURNAL: Proc. Natl. Acad. Sci. U.S.A.
        (D) VOLUME: 86
        (F) PAGES: 4554-4558
        (G) DATE: 1989

(xi) SEQUENCE DESCRIPTION: SEQ ID NO:14:
```

Met Arg Lys Met Gln Lys Glu Ile Leu Ser Val Leu Gly Pro Pro His
1               5                   10                  15

Arg Pro Arg Pro Leu His Gly Leu Gln Gln Pro Gln Pro Pro Val Leu
            20                  25                  30

Pro Pro Gln Gln Gln Gln Gln Gln Gln Gln Gln Thr Ala Asp Glu
        35                  40                  45

Glu Pro Pro Gly Arg Leu Lys Ser Ala Pro Leu Phe Met Leu Asp
50              55                  60

Leu Tyr Asn Ala Leu Ser Asn Asp Asp Glu Glu Asp Gly Ala Ser Glu
65                  70                  75                  80

Gly Val Gly Gln Glu Pro Gly Ser His Gly Gly Ala Ser Ser Ser Gln
                85                  90                  95

Leu Arg Gln Pro Ser Pro Gly Ala Ala His Ser Leu Asn Arg Lys Ser
            100                 105                 110

Leu Leu Ala Pro Gly Pro Gly Gly Ala Ser Pro Leu Thr Ser Ala
            115                 120                 125

Gln Asp Ser Ala Phe Leu Asn Asp Ala Asp Met Val Met Ser Phe Val
130                 135                 140

Asn Leu Val Gly Tyr Asp Lys Glu Phe Ser Pro His Gln Arg His His
145                 150                 155                 160

Lys Glu Phe Lys Phe Asn Leu Ser Gln Ile Pro Glu Gly Glu Ala Val
                165                 170                 175

Thr Ala Ala Glu Phe Arg Val Tyr Lys Asp Cys Val Val Gly Ser Phe
            180                 185                 190

Lys Asn Gln Thr Phe Leu Ile Ser Ile Tyr Gln Val Leu Gln Glu Ala
            195                 200                 205

Gln His Arg Asp Ser Asp Leu Phe Leu Leu Asp Thr Arg Val Val Trp
210                 215                 220

Ala Ser Glu Glu Gly Trp Leu Glu Phe Asp Ile Thr Ala Thr Ser Asn
225                 230                 235                 240

Leu Trp Val Val Ile Pro Gln His Asn Met Gly Leu Gln Leu Ser Val
                245                 250                 255

Val Thr Arg Asp Gly Leu His Val Asn Pro Arg Ala Ala Gly Leu Val
            260                 265                 270

Gly Arg Asp Gly Pro Tyr Asp Lys Gln Pro Phe Met Val Ala Phe Phe
            275                 280                 285

Lys Val Ser Glu Val His Val Arg Thr Thr Arg Ser Ala Ser Ser Arg
290                 295                 300

```
Arg Arg Gln Gln Ser Arg Asn Arg Ser Thr Gln Ser Gln Asp Val Ser
305                 310                 315                 320

Arg Gly Ser Gly Ser Ser Asp Tyr Asn Gly Ser Glu Leu Lys Thr Ala
            325                 330                 335

Cys Lys Lys His Glu Leu Tyr Val Ser Phe Gln Asp Leu Gly Trp Gln
            340                 345                 350

Asp Trp Ile Ile Ala Pro Lys Gly Tyr Ala Ala Asn Tyr Cys Asp Gly
            355                 360                 365

Glu Cys Ser Phe Pro Leu Asn Ala His Met Asn Ala Thr Asn His Ala
370                 375                 380

Ile Val Gln Thr Leu Val His Leu Met Asn Pro Glu Thr Val Pro Lys
385                 390                 395                 400

Pro Cys Cys Ala Pro Thr Lys Leu Asn Ala Ile Ser Val Leu Tyr Phe
            405                 410                 415

Asp Asp Asn Ser Asn Val Ile Leu Lys Lys Tyr Arg Asn Met Val Val
            420                 425                 430

Arg Ala Cys Gly Cys His
            435

(2) INFORMATION FOR SEQ ID NO:15:

(i) SEQUENCE CHARACTERISTICS:
        (A) LENGTH: 372 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..372
        (D) OTHER INFORMATION: /note= "PRE-PRO-GDF-1"

(x) PUBLICATION INFORMATION:
        (A) AUTHORS: LEE,
        (B) TITLE: EXPRESSION OF GROWTH/DIFFERENTIATION FACTOR 1
        (C) JOURNAL: Proc. Natl. Acad. Sci. U.S.A.
        (D) VOLUME: 88
        (F) PAGES: 4250-4254
        (G) DATE: MAY-1991

(xi) SEQUENCE DESCRIPTION: SEQ ID NO:15:

Met Pro Pro Pro Gln Gln Gly Pro Cys Gly His His Leu Leu Leu Leu
1               5                   10                  15

Leu Ala Leu Leu Leu Pro Ser Leu Pro Leu Thr Arg Ala Pro Val Pro
            20                  25                  30

Pro Gly Pro Ala Ala Ala Leu Leu Gln Ala Leu Gly Leu Arg Asp Glu
            35                  40                  45

Pro Gln Gly Ala Pro Arg Leu Arg Pro Val Pro Pro Val Met Trp Arg
50                  55                  60

Leu Phe Arg Arg Arg Asp Pro Gln Glu Thr Arg Ser Gly Ser Arg Arg
65                  70                  75                  80

Thr Ser Pro Gly Val Thr Leu Gln Pro Cys His Val Glu Glu Leu Gly
            85                  90                  95

Val Ala Gly Asn Ile Val Arg His Ile Pro Asp Arg Gly Ala Pro Thr
            100                 105                 110

Arg Ala Ser Glu Pro Val Ser Ala Ala Gly His Cys Pro Glu Trp Thr
            115                 120                 125

Val Val Phe Asp Leu Ser Ala Val Glu Pro Ala Glu Arg Pro Ser Arg
130                 135                 140
```

```
Ala Arg Leu Glu Leu Arg Phe Ala Ala Ala Ala Ala Pro Glu
145                 150                 155                 160

Gly Gly Trp Glu Leu Ser Val Ala Gln Ala Gly Gln Gly Ala Gly Ala
                165                 170                 175

Asp Pro Gly Pro Val Leu Leu Arg Gln Leu Val Pro Ala Leu Gly Pro
                180                 185                 190

Pro Val Arg Ala Glu Leu Leu Gly Ala Ala Trp Ala Arg Asn Ala Ser
                195                 200                 205

Trp Pro Arg Ser Leu Arg Leu Ala Leu Ala Leu Arg Pro Arg Ala Pro
210                 215                 220

Ala Ala Cys Ala Arg Leu Ala Glu Ala Ser Leu Leu Leu Val Thr Leu
225                 230                 235                 240

Asp Pro Arg Leu Cys His Pro Leu Ala Arg Pro Arg Arg Asp Ala Glu
                245                 250                 255

Pro Val Leu Gly Gly Gly Pro Gly Gly Ala Cys Arg Ala Arg Arg Leu
                260                 265                 270

Tyr Val Ser Phe Arg Glu Val Gly Trp His Arg Trp Val Ile Ala Pro
                275                 280                 285

Arg Gly Phe Leu Ala Asn Tyr Cys Gln Gly Gln Cys Ala Leu Pro Val
290                 295                 300

Ala Leu Ser Gly Ser Gly Gly Pro Pro Ala Leu Asn His Ala Val Leu
305                 310                 315                 320

Arg Ala Leu Met His Ala Ala Ala Pro Gly Ala Ala Asp Leu Pro Cys
                325                 330                 335

Cys Val Pro Ala Arg Leu Ser Pro Ile Ser Val Leu Phe Phe Asp Asn
                340                 345                 350

Ser Asp Asn Val Val Leu Arg Gln Tyr Glu Asp Met Val Val Asp Glu
                355                 360                 365

Cys Gly Cys Arg
        370

(2) INFORMATION FOR SEQ ID NO:16:

(i) SEQUENCE CHARACTERISTICS:
        (A) LENGTH: 455 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..455
        (D) OTHER INFORMATION: /note= "PRE-PRO 60A"

(x) PUBLICATION INFORMATION:
        (A) AUTHORS: WHARTON,
        (C) JOURNAL: Proc. Natl. Acad. Sci. U.S.A.
        (D) VOLUME: 88
        (F) PAGES: 9214-9218
        (G) DATE: 1991

(xi) SEQUENCE DESCRIPTION: SEQ ID NO:16:

Met Ser Gly Leu Arg Asn Thr Ser Glu Ala Val Ala Val Leu Ala Ser
1               5                   10                  15

Leu Gly Leu Gly Met Val Leu Leu Met Phe Val Ala Thr Thr Pro Pro
                20                  25                  30

Ala Val Glu Ala Thr Gln Ser Gly Ile Tyr Ile Asp Asn Gly Lys Asp
                35                  40                  45
```

-continued

```
Gln Thr Ile Met His Arg Val Leu Ser Glu Asp Asp Lys Leu Asp Val
    50                      55                  60

Ser Tyr Glu Ile Leu Glu Phe Leu Gly Ile Ala Glu Arg Pro Thr His
65                      70                  75                  80

Leu Ser Ser His Gln Leu Ser Leu Arg Lys Ser Ala Pro Lys Phe Leu
                85                  90                  95

Leu Asp Val Tyr His Arg Ile Thr Ala Glu Glu Gly Leu Ser Asp Gln
            100                 105                 110

Asp Glu Asp Asp Tyr Glu Arg Gly His Arg Ser Arg Arg Ser Ala
            115                 120                 125

Asp Leu Glu Glu Asp Glu Gly Glu Gln Gln Lys Asn Phe Ile Thr Asp
    130                 135                 140

Leu Asp Lys Arg Ala Ile Asp Glu Ser Asp Ile Ile Met Thr Phe Leu
145                 150                 155                 160

Asn Lys Arg His His Asn Val Asp Glu Leu Arg His Glu His Gly Arg
                165                 170                 175

Arg Leu Trp Phe Asp Val Ser Asn Val Pro Asn Asp Asn Tyr Leu Val
            180                 185                 190

Met Ala Glu Leu Arg Ile Tyr Gln Asn Ala Asn Glu Gly Lys Trp Leu
    195                 200                 205

Thr Ala Asn Arg Glu Phe Thr Ile Thr Val Tyr Ala Ile Gly Thr Gly
    210                 215                 220

Thr Leu Gly Gln His Thr Met Glu Pro Leu Ser Ser Val Asn Thr Thr
225                 230                 235                 240

Gly Asp Tyr Val Gly Trp Leu Glu Leu Asn Val Thr Glu Gly Leu His
            245                 250                 255

Glu Trp Leu Val Lys Ser Lys Asp Asn His Gly Ile Tyr Ile Gly Ala
            260                 265                 270

His Ala Val Asn Arg Pro Asp Arg Glu Val Lys Leu Asp Asp Ile Gly
    275                 280                 285

Leu Ile His Arg Lys Val Asp Asp Glu Phe Gln Pro Phe Met Ile Gly
    290                 295                 300

Phe Phe Arg Gly Pro Glu Leu Ile Lys Ala Thr Ala His Ser Ser His
305                 310                 315                 320

His Arg Ser Lys Arg Ser Ala Ser His Pro Arg Lys Arg Lys Lys Ser
                325                 330                 335

Val Ser Pro Asn Asn Val Pro Leu Leu Glu Pro Met Glu Ser Thr Arg
            340                 345                 350

Ser Cys Gln Met Gln Thr Leu Tyr Ile Asp Phe Lys Asp Leu Gly Trp
        355                 360                 365

His Asp Trp Ile Ile Ala Pro Glu Gly Tyr Gly Ala Phe Tyr Cys Ser
    370                 375                 380

Gly Glu Cys Asn Phe Pro Leu Asn Ala His Met Asn Ala Thr Asn His
385                 390                 395                 400

Ala Ile Val Gln Thr Leu Val His Leu Leu Glu Pro Lys Lys Val Pro
                405                 410                 415

Lys Pro Cys Cys Ala Pro Thr Arg Leu Gly Ala Leu Pro Val Leu Tyr
            420                 425                 430

His Leu Asn Asp Glu Asn Val Asn Leu Lys Lys Tyr Arg Asn Met Ile
            435                 440                 445

Val Lys Ser Cys Gly Cys His
    450                 455
```

(2) INFORMATION FOR SEQ ID NO:17:

(i) SEQUENCE CHARACTERISTICS:
        (A) LENGTH: 472 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..472
        (D) OTHER INFORMATION: /note= "PRE-PRO-BMP3"

(x) PUBLICATION INFORMATION:
        (A) AUTHORS: WOZNEY,
        (C) JOURNAL: SCIENCE
        (D) VOLUME: 242
        (F) PAGES: 1528-1534
        (G) DATE: 1988

(xi) SEQUENCE DESCRIPTION: SEQ ID NO:17:

```
Met Ala Gly Ala Ser Arg Leu Leu Phe Leu Trp Leu Gly Cys Phe Cys
 1               5                  10                  15

Val Ser Leu Ala Gln Gly Glu Arg Pro Lys Pro Phe Pro Glu Leu
             20                  25                  30

Arg Lys Ala Val Pro Gly Asp Arg Thr Ala Gly Gly Gly Pro Asp Ser
             35                  40                  45

Glu Leu Gln Pro Gln Asp Lys Val Ser Glu His Met Leu Arg Leu Tyr
         50                  55                  60

Asp Arg Tyr Ser Thr Val Gln Ala Ala Arg Thr Pro Gly Ser Leu Glu
65                  70                  75                  80

Gly Gly Ser Gln Pro Trp Arg Pro Arg Leu Leu Arg Glu Gly Asn Thr
                 85                  90                  95

Val Arg Ser Phe Arg Ala Ala Ala Glu Thr Leu Glu Arg Lys Gly
                100                 105                 110

Leu Tyr Ile Phe Asn Leu Thr Ser Leu Thr Lys Ser Glu Asn Ile Leu
            115                 120                 125

Ser Ala Thr Leu Tyr Phe Cys Ile Gly Glu Leu Gly Asn Ile Ser Leu
130                 135                 140

Ser Cys Pro Val Ser Gly Gly Cys Ser His His Ala Gln Arg Lys His
145                 150                 155                 160

Ile Gln Ile Asp Leu Ser Ala Trp Thr Leu Lys Phe Ser Arg Asn Gln
                165                 170                 175

Ser Gln Leu Leu Gly His Leu Ser Val Asp Met Ala Lys Ser His Arg
            180                 185                 190

Asp Ile Met Ser Trp Leu Ser Lys Asp Ile Thr Gln Phe Leu Arg Lys
        195                 200                 205

Ala Lys Glu Asn Glu Glu Phe Leu Ile Gly Phe Asn Ile Thr Ser Lys
210                 215                 220

Gly Arg Gln Leu Pro Lys Arg Arg Leu Pro Phe Pro Glu Pro Tyr Ile
225                 230                 235                 240

Leu Val Tyr Ala Asn Asp Ala Ala Ile Ser Glu Pro Glu Ser Val Val
                245                 250                 255

Ser Ser Leu Gln Gly His Arg Asn Phe Pro Thr Gly Thr Val Pro Lys
            260                 265                 270

Trp Asp Ser His Ile Arg Ala Ala Leu Ser Ile Glu Arg Arg Lys Lys
        275                 280                 285
```

```
Arg Ser Thr Gly Val Leu Leu Pro Leu Gln Asn Asn Glu Leu Pro Gly
    290                 295                 300

Ala Glu Tyr Gln Tyr Lys Lys Asp Glu Val Trp Glu Arg Lys Pro
305                 310                 315                 320

Tyr Lys Thr Leu Gln Ala Gln Ala Pro Glu Lys Ser Lys Asn Lys Lys
                325                 330                 335

Lys Gln Arg Lys Gly Pro His Arg Lys Ser Gln Thr Leu Gln Phe Asp
                340                 345                 350

Glu Gln Thr Leu Lys Lys Ala Arg Arg Lys Gln Trp Ile Glu Pro Arg
                355                 360                 365

Asn Cys Ala Arg Arg Tyr Leu Lys Val Asp Phe Ala Asp Ile Gly Trp
                370                 375                 380

Ser Glu Trp Ile Ile Ser Pro Lys Ser Phe Asp Ala Tyr Tyr Cys Ser
385                 390                 395                 400

Gly Ala Cys Gln Phe Pro Met Pro Lys Ser Leu Lys Pro Ser Asn His
                405                 410                 415

Ala Thr Ile Gln Ser Ile Val Arg Ala Val Gly Val Val Pro Gly Ile
                420                 425                 430

Pro Glu Pro Cys Cys Val Pro Glu Lys Met Ser Ser Leu Ser Ile Leu
                435                 440                 445

Phe Phe Asp Glu Asn Lys Asn Val Val Leu Lys Val Tyr Pro Asn Met
    450                 455                 460

Thr Val Glu Ser Cys Ala Cys Arg
465                 470

(2) INFORMATION FOR SEQ ID NO:18:

(i) SEQUENCE CHARACTERISTICS:
        (A) LENGTH: 453 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..453
        (D) OTHER INFORMATION: /note= "PRE-PRO-BMP5 (HUMAN)"

(x) PUBLICATION INFORMATION:
        (A) AUTHORS: CELESTE,
        (C) JOURNAL: Proc. Natl. Acad. Sci. U.S.A.
        (D) VOLUME: 87
        (F) PAGES: 9843-9847
        (G) DATE: 1991

(xi) SEQUENCE DESCRIPTION: SEQ ID NO:18:

Met His Leu Thr Val Phe Leu Leu Lys Gly Ile Val Gly Phe Leu Trp
1                   5                   10                  15

Ser Cys Trp Val Leu Val Gly Tyr Ala Lys Gly Gly Leu Gly Asp Asn
                20                  25                  30

His Val His Ser Ser Phe Ile Tyr Arg Arg Leu Arg Asn His Glu Arg
            35                  40                  45

Arg Glu Ile Gln Arg Glu Ile Leu Ser Ile Leu Gly Leu Pro His Arg
            50                  55                  60

Pro Arg Pro Phe Ser Pro Gly Lys Gln Ala Ser Ser Ala Pro Leu Phe
65                  70                  75                  80

Met Leu Asp Leu Tyr Asn Ala Met Thr Asn Glu Glu Asn Pro Glu Glu
                85                  90                  95
```

```
Ser Glu Tyr Ser Val Arg Ala Ser Leu Ala Glu Glu Thr Arg Gly Ala
            100                 105                 110

Arg Lys Gly Tyr Pro Ala Ser Pro Asn Gly Tyr Pro Arg Arg Ile Gln
            115                 120                 125

Leu Ser Arg Thr Thr Pro Leu Thr Thr Gln Ser Pro Pro Leu Ala Ser
            130                 135                 140

Leu His Asp Thr Asn Phe Leu Asn Asp Ala Asp Met Val Met Ser Phe
145                 150                 155                 160

Val Asn Leu Val Glu Arg Asp Lys Asp Phe Ser His Gln Arg Arg His
                165                 170                 175

Tyr Lys Glu Arg Phe Asp Leu Thr Gln Ile Pro His Gly Glu Ala Val
            180                 185                 190

Thr Ala Ala Glu Phe Arg Ile Tyr Lys Asp Arg Ser Asn Asn Arg Phe
            195                 200                 205

Glu Asn Glu Thr Ile Lys Ile Ser Ile Tyr Gln Ile Ile Lys Glu Tyr
            210                 215                 220

Thr Asn Arg Asp Ala Asp Leu Phe Leu Leu Asp Thr Arg Lys Ala Gln
225                 230                 235                 240

Ala Leu Asp Val Gly Trp Leu Val Phe Asp Ile Thr Val Thr Ser Asn
                245                 250                 255

His Trp Val Ile Asn Pro Gln Asn Asn Leu Gly Leu Gln Leu Cys Ala
            260                 265                 270

Glu Thr Gly Asp Gly Arg Ser Ile Asn Val Lys Ser Ala Gly Leu Val
            275                 280                 285

Gly Arg Gln Gly Pro Gln Ser Lys Gln Pro Phe Met Val Ala Phe Phe
            290                 295                 300

Lys Ala Ser Glu Val Leu Leu Arg Ser Val Arg Ala Ala Asn Lys Arg
305                 310                 315                 320

Lys Asn Gln Asn Arg Asn Lys Ser Ser Ser His Gln Asp Ser Ser Arg
                325                 330                 335

Met Ser Ser Val Gly Asp Tyr Asn Thr Ser Glu Gln Lys Gln Ala Cys
            340                 345                 350

Lys Lys His Glu Leu Tyr Val Ser Phe Arg Asp Leu Gly Trp Gln Asp
            355                 360                 365

Trp Ile Ile Ala Pro Glu Gly Tyr Ala Ala Phe Tyr Cys Asp Gly Glu
            370                 375                 380

Cys Ser Phe Pro Leu Asn Ala His Met Asn Ala Thr Asn His Ala Ile
385                 390                 395                 400

Val Gln Thr Leu Val His Leu Met Phe Pro Asp His Val Pro Lys Pro
                405                 410                 415

Cys Cys Ala Pro Thr Lys Leu Asn Ala Ile Ser Val Leu Tyr Phe Asp
            420                 425                 430

Asp Ser Ser Asn Val Ile Leu Lys Lys Tyr Arg Asn Met Val Val Arg
            435                 440                 445

Ser Cys Gly Cys His
            450

(2) INFORMATION FOR SEQ ID NO:19:

(i) SEQUENCE CHARACTERISTICS:
        (A) LENGTH: 513 amino acids
        (B) TYPE: amino acid
        (C) STRANDEDNESS: single
        (D) TOPOLOGY: linear (ii) MOLECULE TYPE: protein
```

```
    (ix) FEATURE:
         (A) NAME/KEY: Protein
         (B) LOCATION: 1..513
         (D) OTHER INFORMATION: /note= "PRE-PRO-BMP6 (HUMAN)"

(x) PUBLICATION INFORMATION:
         (A) AUTHORS: CELESTE,
         (C) JOURNAL: Proc. Natl. Acad. Sci. U.S.A.
         (D) VOLUME: 87
         (F) PAGES: 9843-9847
         (G) DATE: 1991

(xi) SEQUENCE DESCRIPTION: SEQ ID NO:19:

Met Pro Gly Leu Gly Arg Arg Ala Gln Trp Leu Cys Trp Trp Trp Gly
1               5                   10                  15

Leu Leu Cys Ser Cys Cys Gly Pro Pro Leu Arg Pro Pro Leu Pro
                20                  25                  30

Ala Ala Ala Ala Ala Ala Ala Gly Gly Gln Leu Leu Gly Asp Gly Gly
            35                  40                  45

Ser Pro Gly Arg Thr Glu Gln Pro Pro Ser Pro Gln Ser Ser Ser
    50                  55                  60

Gly Phe Leu Tyr Arg Arg Leu Lys Thr Gln Glu Lys Arg Glu Met Gln
65                  70                  75                  80

Lys Glu Ile Leu Ser Val Leu Gly Leu Pro His Arg Pro Arg Pro Leu
                85                  90                  95

His Gly Leu Gln Gln Pro Gln Pro Pro Ala Leu Arg Gln Gln Glu Glu
                100                 105                 110

Gln Gln Gln Gln Gln Gln Leu Pro Arg Gly Glu Pro Pro Pro Gly Arg
                115                 120                 125

Leu Lys Ser Ala Pro Leu Phe Met Leu Asp Leu Tyr Asn Ala Leu Ser
    130                 135                 140

Ala Asp Asn Asp Glu Asp Gly Ala Ser Glu Gly Glu Arg Gln Gln Ser
145                 150                 155                 160

Trp Pro His Glu Ala Ala Ser Ser Ser Gln Arg Arg Gln Pro Pro Pro
                165                 170                 175

Gly Ala Ala His Pro Leu Asn Arg Lys Ser Leu Leu Ala Pro Gly Ser
                180                 185                 190

Gly Ser Gly Gly Ala Ser Pro Leu Thr Ser Ala Gln Asp Ser Ala Phe
    195                 200                 205

Leu Asn Asp Ala Asp Met Val Met Ser Phe Val Asn Leu Val Glu Tyr
    210                 215                 220

Asp Lys Glu Phe Ser Pro Arg Gln Arg His His Lys Glu Phe Lys Phe
225                 230                 235                 240

Asn Leu Ser Gln Ile Pro Glu Gly Glu Val Val Thr Ala Ala Glu Phe
                245                 250                 255

Arg Ile Tyr Lys Asp Cys Val Met Gly Ser Phe Lys Asn Gln Thr Phe
                260                 265                 270

Leu Ile Ser Ile Tyr Gln Val Leu Gln Glu His Gln His Arg Asp Ser
    275                 280                 285

Asp Leu Phe Leu Leu Asp Thr Arg Val Val Trp Ala Ser Glu Glu Gly
    290                 295                 300

Trp Leu Glu Phe Asp Ile Thr Ala Thr Ser Asn Leu Trp Val Val Thr
305                 310                 315                 320

Pro Gln His Asn Met Gly Leu Gln Leu Ser Val Thr Arg Asp Gly
                325                 330                 335

Val His Val His Pro Arg Ala Ala Gly Leu Val Gly Arg Asp Gly Pro
```

-continued

```
                340                 345                 350
Tyr Asp Lys Gln Pro Phe Met Val Ala Phe Phe Lys Val Ser Glu Val
                355                 360                 365

His Val Arg Thr Thr Arg Ser Ala Ser Ser Arg Arg Gln Gln Ser
    370                 375                 380

Arg Asn Arg Ser Thr Gln Ser Gln Asp Val Ala Arg Val Ser Ser Ala
385                 390                 395                 400

Ser Asp Tyr Asn Ser Ser Glu Leu Lys Thr Ala Cys Arg Lys His Glu
                405                 410                 415

Leu Tyr Val Ser Phe Gln Asp Leu Gly Trp Gln Asp Trp Ile Ile Ala
                420                 425                 430

Pro Lys Gly Tyr Ala Ala Asn Tyr Cys Asp Gly Glu Cys Ser Phe Pro
                435                 440                 445

Leu Asn Ala His Met Asn Ala Thr Asn His Ala Ile Val Gln Thr Leu
                450                 455                 460

Val His Leu Met Asn Pro Glu Tyr Val Pro Lys Pro Cys Cys Ala Pro
465                 470                 475                 480

Thr Lys Leu Asn Ala Ile Ser Val Leu Tyr Phe Asp Asp Asn Ser Asn
                485                 490                 495

Val Ile Leu Lys Lys Tyr Arg Asn Met Val Val Arg Ala Cys Gly Cys
                500                 505                 510

His
```

(2) INFORMATION FOR SEQ ID NO:20:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..97
        (D) OTHER INFORMATION: /label= Generic-Seq-7
            /note= "wherein each Xaa is independently selected
            from a group of one or more specified amino acids
            as defined in the specification."

(xi) SEQUENCE DESCRIPTION: SEQ ID NO:20:

```
Leu Xaa Xaa Xaa Phe Xaa Xaa Xaa Gly Trp Xaa Xaa Xaa Xaa Xaa Xaa
1               5                   10                  15

Pro Xaa Xaa Xaa Xaa Ala Xaa Tyr Cys Xaa Gly Xaa Cys Xaa Xaa Pro
                20                  25                  30

Xaa Xaa Xaa Xaa Xaa Xaa Xaa Xaa Asn His Ala Xaa Xaa Xaa Xaa Xaa
                35                  40                  45

Xaa Xaa Xaa Xaa Xaa Xaa Xaa Xaa Xaa Xaa Xaa Xaa Cys Cys Xaa Pro
        50                  55                  60

Xaa Xaa Xaa Xaa Xaa Xaa Xaa Xaa Leu Xaa Xaa Xaa Xaa Xaa Xaa Xaa
65                  70                  75                  80

Val Xaa Leu Xaa Xaa Xaa Xaa Xaa Met Xaa Val Xaa Xaa Cys Xaa Cys
                85                  90                  95

Xaa
```

(2) INFORMATION FOR SEQ ID NO:21:

(i) SEQUENCE CHARACTERISTICS:

-continued (A) LENGTH: 102 amino acids
(B) TYPE: amino acid
(C) STRANDEDNESS: single
(D) TOPOLOGY: linear (ii) MOLECULE TYPE: protein (ix) FEATURE:
(A) NAME/KEY: Protein
(B) LOCATION: 1..102
(D) OTHER INFORMATION: /label= Generic-Seq-8
/note= "wherin each Xaa is independently selected from a group of one or more specified amino acids as defined in the specification."

(xi) SEQUENCE DESCRIPTION: SEQ ID NO:21:

```
Cys Xaa Xaa Xaa Xaa Leu Xaa Xaa Xaa Phe Xaa Xaa Xaa Gly Trp Xaa
1               5                   10                  15

Xaa Xaa Xaa Xaa Xaa Pro Xaa Xaa Xaa Xaa Ala Xaa Tyr Cys Xaa Gly
            20                  25                  30

Xaa Cys Xaa Xaa Pro Xaa Xaa Xaa Xaa Xaa Xaa Xaa Xaa Asn His Ala
        35                  40                  45

Xaa Xaa Xaa Xaa Xaa Xaa Xaa Xaa Xaa Xaa Xaa Xaa Xaa Xaa Xaa Xaa
    50                  55                  60

Xaa Cys Cys Xaa Pro Xaa Xaa Xaa Xaa Xaa Xaa Xaa Xaa Leu Xaa Xaa
65                  70                  75                  80

Xaa Xaa Xaa Xaa Xaa Val Xaa Leu Xaa Xaa Xaa Xaa Xaa Met Xaa Val
                85                  90                  95

Xaa Xaa Cys Xaa Cys Xaa
            100
```

(2) INFORMATION FOR SEQ ID NO:22:

(i) SEQUENCE CHARACTERISTICS:
(A) LENGTH: 102 amino acids
(B) TYPE: amino acid
(D) TOPOLOGY: linear (ii) MOLECULE TYPE: protein (ix) FEATURE:
(A) NAME/KEY: Protein
(B) LOCATION: 1..102
(D) OTHER INFORMATION: /label= OPX
/note= "WHEREIN EACH XAA IS INDEPENDENTLY SELECTED FROM A GROUP OF ONE OR MORE SPECIFIED AMINO ACIDS AS DEFINED IN THE SPECIFICATION (SECTION I)"

(xi) SEQUENCE DESCRIPTION: SEQ ID NO:22:

```
Cys Xaa Xaa His Glu Leu Tyr Val Xaa Phe Xaa Asp Leu Gly Trp Xaa
1               5                   10                  15

Asp Trp Xaa Ile Ala Pro Xaa Gly Tyr Xaa Ala Tyr Tyr Cys Glu Gly
            20                  25                  30

Glu Cys Xaa Phe Pro Leu Xaa Ser Xaa Met Asn Ala Thr Asn His Ala
        35                  40                  45

Ile Xaa Gln Xaa Leu Val His Xaa Xaa Xaa Pro Xaa Xaa Val Pro Lys
    50                  55                  60

Xaa Cys Cys Ala Pro Thr Xaa Leu Xaa Ala Xaa Ser Val Leu Tyr Xaa
65                  70                  75                  80

Asp Xaa Ser Xaa Asn Val Xaa Leu Xaa Lys Xaa Arg Asn Met Val Val
                85                  90                  95

Xaa Ala Cys Gly Cys His
            100
```

```
(2) INFORMATION FOR SEQ ID NO:23:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Cleavage-site
        (B) LOCATION: 1..4
        (D) OTHER INFORMATION: /note= "PROTEOLYTIC CLEAVAGE SITE"

(xi) SEQUENCE DESCRIPTION: SEQ ID NO:23:

Arg Xaa Xaa Arg
```